US012793141B1

(12) United States Patent
Perros et al.

(10) Patent No.: US 12,793,141 B1
(45) Date of Patent: Nov. 10, 2026

(54) MACHINE-LEARNING TECHNIQUES FOR ANOMALY DETECTION IN HEALTHCARE

(71) Applicant: Magnum Transaction Sub, LLC, Newtown Square, PA (US)

(72) Inventors: Ioakeim Perros, San Jose, CA (US); Bangyi Chen, Fremont, CA (US); Zeeshan Syed, Cupertino, CA (US)

(73) Assignee: Magnum Transaction Sub, LLC, Newtown Square, PA (US)

( * ) Notice: Subject to any disclaimer, the term of this patent is extended or adjusted under 35 U.S.C. 154(b) by 1022 days.

(21) Appl. No.: 17/327,463

(22) Filed: May 21, 2021

Related U.S. Application Data

(60) Provisional application No. 63/030,229, filed on May 26, 2020.

(51) Int. Cl.
*G06Q 40/08* (2012.01)
*G06F 16/00* (2019.01)
*G06N 20/00* (2019.01)
*G16H 40/00* (2018.01)

(52) U.S. Cl.
CPC ............. *G06Q 40/08* (2013.01); *G06F 16/00* (2019.01); *G06N 20/00* (2019.01); *G16H 40/00* (2018.01)

(58) Field of Classification Search
CPC ........ G06Q 40/08; G16H 40/00; G06N 20/00; G06F 16/00
See application file for complete search history.

(56) References Cited

U.S. PATENT DOCUMENTS

| | | | |
|---|---|---|---|
| 6,826,536 | B1 | 11/2004 | Forman |
| 7,191,150 | B1 | 3/2007 | Shao |
| 7,853,456 | B2 | 12/2010 | Soto et al. |

(Continued)

FOREIGN PATENT DOCUMENTS

| | | | |
|---|---|---|---|
| CA | 2560934 | A1 | 11/2005 |
| CA | 2715825 | A1 | 8/2009 |

(Continued)

OTHER PUBLICATIONS

Notice of Allowance mailed Jul. 28, 2021, for U.S. Appl. No. 14/678,349, filed Apr. 3, 2015, eleven pages.

(Continued)

*Primary Examiner* — Jennifer N Welch
*Assistant Examiner* — Quoc Ly Phu Phung
(74) *Attorney, Agent, or Firm* — Morrison & Foerster LLP

(57) ABSTRACT

An exemplary method for using machine-learning to detect anomalous healthcare providers comprises: receiving medical data of a plurality of healthcare providers; obtaining a subset of the medical data based on a first care provision type; constructing a first tensor based on the subset of the medical data; executing an unsupervised machine-learning algorithm to decompose the first tensor into a plurality of data structures, wherein the plurality of data structures are indicative of one or more common patterns among the plurality of healthcare providers; reconstructing the first tensor by generating a second tensor using the plurality of data structures; calculating, based on the first tensor and the second tensor, a score for a particular provider of the plurality of providers; and providing a recommendation regarding the particular provider based on the score.

18 Claims, 12 Drawing Sheets

(56) References Cited

U.S. PATENT DOCUMENTS

| | | | | |
|---|---|---|---|---|
| 8,417,541 | B1 | 4/2013 | Kramer | |
| 8,548,937 | B2 | 10/2013 | Saigal et al. | |
| 8,615,405 | B2 * | 12/2013 | Rousso | G16H 30/20 600/431 |
| 9,710,599 | B1 | 7/2017 | Johnson | |
| 9,996,666 | B1 | 6/2018 | Wilson | |
| 10,034,608 | B1 | 7/2018 | Dintenfass | |
| 10,318,710 | B2 | 6/2019 | Veren | |
| 10,743,809 | B1 * | 8/2020 | Kamousi | A61B 5/4848 |
| 10,855,957 | B2 | 12/2020 | Kapoustin | |
| 10,923,231 | B2 | 2/2021 | Kelly | |
| 10,937,108 | B1 | 3/2021 | Tabak | |
| 10,943,676 | B2 | 3/2021 | Farooq et al. | |
| 11,114,204 | B1 | 9/2021 | Guttag et al. | |
| 11,347,829 | B1 | 5/2022 | Sclar | |
| 11,468,998 | B2 | 10/2022 | Koblick | |
| 11,556,737 | B2 * | 1/2023 | Austin | G06V 10/96 |
| 11,568,982 | B1 | 1/2023 | Guttag et al. | |
| 11,610,679 | B1 | 3/2023 | Zhan et al. | |
| 11,862,346 | B1 | 1/2024 | Boussios | |
| 12,080,428 | B1 | 9/2024 | Syed | |
| 12,094,582 | B1 | 9/2024 | Goyal | |
| 2003/0135128 | A1 | 7/2003 | Suffin | |
| 2004/0107088 | A1 | 6/2004 | Budzinski | |
| 2006/0173663 | A1 | 8/2006 | Langheier | |
| 2006/0206359 | A1 | 9/2006 | Stang | |
| 2007/0088577 | A1 | 4/2007 | Carter et al. | |
| 2007/0269804 | A1 | 11/2007 | Liew | |
| 2008/0120138 | A1 | 5/2008 | Morita et al. | |
| 2008/0249820 | A1 | 10/2008 | Pathria | |
| 2009/0093689 | A1 | 4/2009 | Schuppert et al. | |
| 2009/0259550 | A1 | 10/2009 | Mihelich | |
| 2010/0174180 | A1 * | 7/2010 | Rousso | G16H 30/40 600/431 |
| 2010/0184093 | A1 | 7/2010 | Donovan | |
| 2011/0082712 | A1 | 4/2011 | Eberhardt, III | |
| 2011/0119212 | A1 | 5/2011 | De Bruin et al. | |
| 2011/0295621 | A1 | 12/2011 | Farooq et al. | |
| 2011/0307426 | A1 | 12/2011 | Syed et al. | |
| 2012/0041330 | A1 | 2/2012 | Prichep et al. | |
| 2012/0066217 | A1 | 3/2012 | Eder | |
| 2012/0095943 | A1 | 4/2012 | Yankov | |
| 2012/0109683 | A1 | 5/2012 | Ebadollahi | |
| 2012/0179002 | A1 | 7/2012 | Brunetti et al. | |
| 2013/0022953 | A1 | 1/2013 | Van Der Linden | |
| 2013/0085769 | A1 * | 4/2013 | Jost | G16H 10/60 705/2 |
| 2013/0096948 | A1 | 4/2013 | Parkinson | |
| 2013/0185096 | A1 | 7/2013 | Giusti | |
| 2013/0197925 | A1 | 8/2013 | Blue | |
| 2013/0225439 | A1 | 8/2013 | Princen et al. | |
| 2014/0058755 | A1 | 2/2014 | Macoviak | |
| 2014/0058763 | A1 | 2/2014 | Zizzamia | |
| 2014/0108034 | A1 | 4/2014 | Akbay | |
| 2014/0149130 | A1 | 5/2014 | Getchius | |
| 2014/0200824 | A1 | 7/2014 | Pancoska | |
| 2014/0244292 | A1 | 8/2014 | Rosenberg | |
| 2014/0257838 | A1 | 9/2014 | Karra | |
| 2014/0371610 | A1 | 12/2014 | Liu et al. | |
| 2015/0006456 | A1 | 1/2015 | Sudharsan | |
| 2015/0046181 | A1 | 2/2015 | Adjaoute | |
| 2015/0073943 | A1 | 3/2015 | Norris et al. | |
| 2015/0081324 | A1 * | 3/2015 | Adjaoute | G06Q 40/08 705/2 |
| 2015/0100336 | A1 | 4/2015 | Ford et al. | |
| 2015/0100349 | A1 | 4/2015 | Lacy et al. | |
| 2015/0161331 | A1 | 6/2015 | Oleynik | |
| 2015/0164453 | A1 | 6/2015 | Choi et al. | |
| 2015/0248534 | A1 | 9/2015 | Krzywicki et al. | |
| 2015/0278470 | A1 | 10/2015 | Bakker | |
| 2015/0289795 | A1 | 10/2015 | Batlle Gómez | |
| 2015/0294075 | A1 | 10/2015 | Rinaldo | |
| 2015/0317449 | A1 | 11/2015 | Eder | |
| 2015/0367145 | A1 | 12/2015 | Sjölund et al. | |
| 2016/0012202 | A1 | 1/2016 | Hu et al. | |
| 2016/0085937 | A1 | 3/2016 | Dettinger | |
| 2016/0125168 | A1 | 5/2016 | Aagesen et al. | |
| 2016/0135706 | A1 | 5/2016 | Sullivan et al. | |
| 2016/0147959 | A1 | 5/2016 | Mariottini et al. | |
| 2016/0196398 | A1 | 7/2016 | Vivero et al. | |
| 2016/0203217 | A1 | 7/2016 | Anisingaraju et al. | |
| 2016/0232310 | A1 | 8/2016 | Dunn | |
| 2016/0259883 | A1 | 9/2016 | Grinchuk et al. | |
| 2016/0378943 | A1 | 12/2016 | Vallée | |
| 2017/0017760 | A1 * | 1/2017 | Freese | G16H 40/63 |
| 2017/0073761 | A1 | 3/2017 | Harkin et al. | |
| 2017/0083682 | A1 | 3/2017 | Mcnutt | |
| 2017/0101093 | A1 | 4/2017 | Barfield, Jr. et al. | |
| 2017/0124269 | A1 | 5/2017 | Mcnair | |
| 2017/0161439 | A1 | 6/2017 | Raduchel | |
| 2017/0168991 | A1 * | 6/2017 | Baskaran | G06F 17/16 |
| 2017/0177822 | A1 | 6/2017 | Fogel | |
| 2017/0185723 | A1 | 6/2017 | Mccallum et al. | |
| 2017/0277856 | A1 | 9/2017 | De La Torre et al. | |
| 2017/0308671 | A1 | 10/2017 | Bahrami et al. | |
| 2017/0316180 | A1 | 11/2017 | Takeda et al. | |
| 2017/0330298 | A1 | 11/2017 | Gregg | |
| 2018/0121619 | A1 | 5/2018 | Perlroth et al. | |
| 2018/0181719 | A1 | 6/2018 | Balian | |
| 2018/0182475 | A1 | 6/2018 | Cossler | |
| 2018/0211013 | A1 | 7/2018 | Courtemanche et al. | |
| 2018/0214105 | A1 | 8/2018 | Anavi et al. | |
| 2018/0271455 | A1 | 9/2018 | Zhong et al. | |
| 2019/0043606 | A1 * | 2/2019 | Roots | G16H 10/60 |
| 2019/0051389 | A1 | 2/2019 | Meittunen et al. | |
| 2019/0172587 | A1 | 6/2019 | Park et al. | |
| 2019/0272209 | A1 * | 9/2019 | Yeung | G06F 3/1234 |
| 2019/0325011 | A1 * | 10/2019 | Saripalli | G06F 11/1004 |
| 2019/0333613 | A1 | 10/2019 | Zaidi et al. | |
| 2019/0371450 | A1 | 12/2019 | Lou et al. | |
| 2020/0020453 | A1 | 1/2020 | Yarbray | |
| 2020/0043070 | A1 | 2/2020 | Ketchel | |
| 2020/0066397 | A1 | 2/2020 | Rai et al. | |
| 2020/0074313 | A1 | 3/2020 | Sharifi Sedeh et al. | |
| 2020/0085369 | A1 * | 3/2020 | Vu | A61B 5/7267 |
| 2020/0342335 | A1 | 10/2020 | Burke | |
| 2020/0388384 | A1 * | 12/2020 | Kunitomi | G16H 70/60 |
| 2021/0020294 | A1 | 1/2021 | Bharmi et al. | |
| 2021/0035693 | A1 | 2/2021 | Mohammad et al. | |
| 2021/0043320 | A1 | 2/2021 | Malkenson | |
| 2021/0050078 | A1 | 2/2021 | Patel | |
| 2021/0064703 | A1 * | 3/2021 | Roy | G06F 40/30 |
| 2021/0065909 | A1 | 3/2021 | Donaldson | |
| 2021/0090748 | A1 | 3/2021 | Toyoshiba et al. | |
| 2021/0098090 | A1 | 4/2021 | Thomas | |
| 2021/0118559 | A1 | 4/2021 | Lefkofsky | |
| 2021/0221404 | A1 | 7/2021 | Reiner et al. | |
| 2021/0249138 | A1 | 8/2021 | Hayashitani et al. | |
| 2021/0296000 | A1 | 9/2021 | Shaw et al. | |
| 2022/0061746 | A1 | 3/2022 | Lyman et al. | |
| 2022/0309592 | A1 | 9/2022 | Zahora | |

FOREIGN PATENT DOCUMENTS

| | | | |
|---|---|---|---|
| EP | 3382584 | A1 | 10/2018 |
| EP | 3500999 | A1 | 6/2019 |
| JP | 2017174406 | A | 9/2017 |
| WO | 2001070094 | A2 | 9/2001 |
| WO | 2015157576 | A1 | 10/2015 |
| WO | 2016044514 | A1 | 3/2016 |
| WO | 2016120955 | A1 | 8/2016 |
| WO | 2017072651 | A1 | 5/2017 |
| WO | 2019212005 | A1 | 11/2019 |
| WO | 2020081609 | A1 | 4/2020 |

OTHER PUBLICATIONS

Final Office Action mailed Jul. 12, 2022, for U.S. Appl. No. 16/853,621, filed Apr. 20, 2020, twenty three pages.

Li, Xiuli et al., "Lung Nodule Malignancy Prediction Using Multi-task Convolutional Neural Network," Proc. of SPIE vol. 10134, 1013424-1 (Year: 2017).

(56) References Cited

OTHER PUBLICATIONS

Ruder, Sebastian. "An Overview of Multi-Task Learning in Deep Neural Networks," https://ruder.io/multi-task/ (Year: 2017).
Bretthauer, K. M., & Cote, M. J. (1998). A model for planning resource requirements in health care organizations. Decision Sciences, 29(1), 243-270. Retrieved from https://search.proquest.com/docview/198106120?accountid=14753 (Year: 1998).
Caruana, Rich. (1997). "Multitask Learning," Kluwer Academic Publishers, Manufactured in the Netherlands, Machine Learning, 35 pages.
Caruana, Rich. (May 1996). "Algorithms and Applications for Multitask Learning," School of Computer Science, Carnegie Mellon University, Pittsburgh, PA, 9 pages.
Final Office Action mailed Dec. 21, 2020, for U.S. Appl. No. 14/622,112, filed Feb. 13, 2015, nine pages.
Final Office Action mailed Dec. 26, 2018, for U.S. Appl. No. 14/809,528, filed Jul. 27, 2015, 30 pages.
Final Office Action mailed Jan. 7, 2019, for U.S. Appl. No. 14/736,470, filed Jun. 11, 2015, fifteen pages.
Final Office Action mailed Jul. 21, 2020, for U.S. Appl. No. 14/678,349, filed Apr. 3, 2015, twelve pages.
Final Office Action mailed Jul. 21, 2020, for U.S. Appl. No. 14/809,528, filed Jul. 27, 2015, twenty pages.
Final Office Action mailed Jul. 23, 2018, for U.S. Appl. No. 14/622,112, filed Feb. 13, 2015, eleven pages.
Final Office Action mailed May 3, 2018, for U.S. Appl. No. 14/678,349, filed Apr. 3, 2015, twenty one pages.
Final Office Action mailed Nov. 16, 2020, for U.S. Appl. No. 14/736,470, filed Jun. 11, 2015, eleven pages.
Non-Final Office Action mailed Dec. 18, 2019, for U.S. Appl. No. 14/678,349, filed Apr. 3, 2015, eleven pages.
Non-Final Office Action mailed Feb. 26, 2018, for U.S. Appl. No. 14/736,470, filed Jun. 11, 2015, sixteen pages.
Non-Final Office Action mailed Jan. 10, 2019, for U.S. Appl. No. 14/678,349, filed Apr. 3, 2015, twenty two pages.
Non-Final Office Action mailed Jan. 29, 2020, for U.S. Appl. No. 14/809,528, filed Jul. 27, 2015, 20 pages.
Non-Final Office Action mailed Jan. 29, 2021, for U.S. Appl. No. 14/678,349, filed Apr. 3, 2015, eight pages.
Non-Final Office Action mailed Mar. 14, 2019, for U.S. Appl. No. 14/622,112, filed Feb. 13, 2015, ten pages.
Non-Final Office Action mailed Mar. 27, 2020, for U.S. Appl. No. 14/622,112, filed Feb. 13, 2015, nine pages.
Non-Final Office Action mailed Mar. 9, 2020, for U.S. Appl. No. 14/736,470, filed Jun. 11, 2015, nine pages.
Non-Final Office Action mailed May 1, 2018, for U.S. Appl. No. 14/809,528, filed Jul. 27, 2015, 25 pages.
Non-Final Office Action malled Sep. 22, 2017, for U.S. Appl. No. 14/678,349, filed Apr. 3, 2015, thirteen pages.
Non-Final Office Action mailed Sep. 28, 2017, for U.S. Appl. No. 14/622,112, filed Feb. 13, 2015, fifteen pages.
Non-Final Office Action mailed Aug. 17, 2021, for U.S. Appl. No. 14/622,112, filed Feb. 13, 2015, 11 pages.
Non-Final Office Action mailed Aug. 27, 2021, for U.S. Appl. No. 14/809,528, filed Jul. 27, 2015, 14 pages.
Baechle, C., et al., "Latent topic ensemble learning for hospital readmission cost optimization," European Journal of Operational Research 281 (2020) 517-531. (Year: 2019).
Non-Final Office Action mailed Feb. 8, 2022, for U.S. Appl. No. 16/853,621, filed Apr. 20, 2020, 27 pages.
Rahimian, F., et al., "Predicting the risk of emergency admission with machine learning: Development and validation using linked electronic health records," PLOS Medicine, Nov. 20, 2018, pp. 1-18 (Year: 2018).
Non-Final Office Action mailed Mar. 18, 2022, for U.S. Appl. No. 14/736,470, filed Jun. 11, 2015, 14 pages.
Alvarez Bustins, et al., "Profile of Osteopathic practice in Spain: results from a standardized data collection study (English)", BMC Complementary and Alternative Medicine, 18, 129, Apr. 11, 2018 (Year: 2018).
Arsene, C. T.C. et al. (2012). "Multicentre Study Design in Survival Analysis," 2012 IEEE Symposium on Computational Intelligence in Bioinformatics and Computational Biology (CIBCB), San Diego, CA, USA, 2012, pp. 135-143.
Brakenhoff, T. B., et al. (2018). "Investigating Risk Adjustment Methods for Health Care Provider Profiling When Observations are Scarce or Events Rare". Health Services Insights, vol. 11, 1-10, doi: http://dx.doi.org/10.1177/1178632918785133 , (Year:2018).
Final Office Action mailed Aug. 8, 2024, for U.S. Appl. No. 17/472,383, filed Sep. 10, 2021, eighteen pages.
Final Office Action mailed Feb. 8, 2024, for U.S. Appl. No. 17/398,931, filed Aug. 10, 2021, ten pages.
Final Office Action mailed Jul. 5, 2024, for U.S. Appl. No. 16/875,835, filed May 15, 2020, 75 pages.
Final Office Action mailed May 18, 2023, for U.S. Appl. No. 16/875,835, filed May 15, 2020, fifty-five pages.
Final Office Action mailed Oct. 4, 2022, for U.S. Appl. No. 14/736,470, filed Jun. 11, 2015, thirteen pages.
Herrete, Emily et al. (Jun. 1, 2015). "Data Resource Profile: Clinical Practice Research Datalink (CPRD) (English)", International Journal of Epidemiology, 44(3), 827-836, (Year: 2015).
Modin, Sonja et al. (Jun. 22, 2009). "Family physicians' effort to stay in charge of the medical treatment when patients have home care by district nurses. A grounded theory study (English)", BMC Family Practice, 10, 45, (Year-2009).
Non-Final Office Action mailed Aug. 28, 2025, for U.S. Appl. No. 18/496,733, filed Oct. 27, 2023, 16 pages.
Non-Final Office Action mailed Dec. 13, 2023, for U.S. Appl. No. 17/472,455, filed Sep. 10, 2021, twenty-three pages.
Non-Final Office Action mailed Dec. 14, 2022, for U.S. Appl. No. 14/809,528, filed Jul. 27, 2015, fifteen pages.
Non-Final Office Action mailed Feb. 6, 2024, for U.S. Appl. No. 17/472,383, filed Sep. 10, 2021, thirty-one pages.
Non-Final Office Action mailed Feb. 7, 2024, for U.S. Appl. No. 14/809,528, filed Jul. 27, 2015, seventeen pages.
Non-Final Office Action mailed Jan. 18, 2023, for U.S. Appl. No. 17/392,086, filed Aug. 2, 2021, nineteen pages.
Non-Final Office Action mailed Jan. 31, 2025, for U.S. Appl. No. 14/809,528, filed Jul. 27, 2015, twenty-two pages.
Non-Final Office Action mailed Jul. 20, 2023, for U.S. Appl. No. 17/398,931, filed Aug. 10, 2021, twenty pages.
Non-Final Office Action mailed Jul. 27, 2022, for U.S. Appl. No. 16/875,835, filed May 15, 2020, forty-eight pages.
Non-Final Office Action mailed Sep. 27, 2023, for U.S. Appl. No. 16/875,835, filed May 15, 2020, 73 pages.
Non-Final Office Action mailed Sep. 27, 2024, for U.S. Appl. No. 17/529,162, filed Nov. 17, 2021, thirty-six pages.
Non-Final Office Action mailed Sep. 9, 2024, for U.S. Appl. No. 18/087,733, filed Dec. 22, 2022, forty-one pages.
Notice of Allowance mailed Feb. 2, 2023, for U.S. Appl. No. 16/853,621, filed Apr. 20, 2020, sixteen pages.
Notice of Allowance mailed Jul. 5, 2024, for U.S. Appl. No. 17/472,455, filed Sep. 10, 2021, nine pages.
Notice of Allowance mailed May 1, 2024, for U.S. Appl. No. 17/398,931, filed Aug. 10, 2021, thirteen pages.
Notice of Allowance mailed Nov. 7, 2022, for U.S. Appl. No. 14/622,112, filed Feb. 13, 2015, nine pages.
Notice of Allowance mailed Sep. 6, 2022, for U.S. Appl. No. 14/622,112, filed Feb. 13, 2015, nine pages.
Subhra Shriti Mishra et al. "IoT Health care Monitoring and Tracking: A Survey (English)", 2019 3rd International Conference on Trends in Electronics and Informatics (ICOEI) (pp. 1052-1057), Oct. 25, 2019 (Year: 2019).
Tan, Kar Way. "Dynamic Queue Management for Hospital Emergency Room Services." Order No. 10169843 Singapore Management University (Singapore), 2013. Ann Arbor: ProQuest. Web., Aug. 25, 2022. (Year: 2013).
Wu, C., et al. 2014, "Using Data-Driven Rules to Predict Mortality in Severe Community Acquired Pneumonia," PLOS/One, Apr. 2014, vol. 9, Issue 4, e89053, located at: www.plosone.org.

(56) References Cited

OTHER PUBLICATIONS

Non-Final Office Action mailed Apr. 30, 2026, for U.S. Appl. No. 19/091,715, filed Mar. 26, 2025, 38, pages.

* cited by examiner

Lateral, horizontal, and frontal slides of a 3-way tensor

A rank-1 3-way tensor

| | Provider 1 | Provider 2 | ... | Provider $n$ |
| --- | --- | --- | --- | --- |
| Diagnosis or Procedure 1 | $a_{11}$ | $a_{12}$ | ... | $a_{1n}$ |
| Diagnosis or Procedure 2 | $a_{21}$ | $a_{22}$ | ... | $a_{2n}$ |
| Diagnosis or Procedure 3 | $a_{31}$ | $a_{32}$ | ... | $a_{3n}$ |
| ... | ... | ... | ... | ... |
| Diagnosis or Procedure $m$ | $a_{m1}$ | $a_{m2}$ | ... | $a_{mn}$ |

FIG. 4A

MACHINE-LEARNING TECHNIQUES FOR ANOMALY DETECTION IN HEALTHCARE

CROSS-REFERENCE TO RELATED APPLICATIONS

This application claims benefit of U.S. Provisional Application No. 63/030,229, filed May 26, 2020, the contents of which are incorporated herein by reference in their entirety.

FIELD OF THE INVENTION

The present disclosure relates generally to machine-learning techniques, and more specifically to unsupervised and supervised machine-learning techniques for anomaly detection in healthcare.

BACKGROUND

Fraud in healthcare involves filing dishonest claims in order to gain financial profit. Abuse can involve systematically following practices that are inconsistent with widely accepted medical care. Fraud and abuse in healthcare can lead to patient harm, unnecessary treatments, and excess costs to the healthcare system.

Accordingly, there is a need to identify healthcare fraud and abuse based on health insurance claims data. This way, healthcare fraud and abuse ("FA") can be mitigated, thus preventing patient harm and reducing unnecessary costs.

BRIEF SUMMARY

An exemplary computer-implemented method for automatically detecting anomalous healthcare providers comprises: in a first pipeline corresponding to a first care provision type: constructing, based on the first care provision type, a first data structure based on medical claims data of a plurality of healthcare providers; automatically performing factorization on the first data structure to obtain a set of data structures, wherein the set of data structures is indicative one or more common patterns among the plurality of healthcare providers; automatically, based on the set of data structures, obtaining a second data structure, wherein the second data structure is indicative of deviation by the plurality of healthcare providers from the one or more common patterns; calculating, based on the second data structure, a score for a particular provider of the plurality of providers, wherein the score is indicative of an amount of deviation of the particular provider from the one or more common patterns when providing the first care provision type; causing display of the particular provider based on the score.

In some embodiments, the first data structure comprises a tensor.

In some embodiments, the tensor comprises a multi-dimensional array, wherein each cell is an exact or normalized count for each provider or a combination of providers of the occurrence of a specific combination of care provision characteristics.

In some embodiments, the tensor comprises a three-dimensional array, wherein each (i,j,k) cell is the number of times the k-th provider billed for the j-th procedure code using the i-th principal diagnosis.

In some embodiments, the set of data structures comprises a set of rank-1 tensors.

In some embodiments, the factorization is a CANDECOMP/PARAFAC (CP) tensor factorization.

In some embodiments, the method further comprises: receiving a user input indicative of a specialty, wherein the plurality of providers is selected based on the specialty.

In some embodiments, the second data structure comprises a reconstruction error tensor.

In some embodiments, the method further comprises: identifying a slice of the reconstruction error tensor, wherein the slice corresponds to the particular provider; and calculating the score for the particular provider based on the slice.

In some embodiments, the method further comprises: calculating scores of features (or their co-occurrence with other features) based on the slice.

In some embodiments, the score is a maximum value of the slice, an average of the slice, or a combination thereof.

In some embodiments, the first data structure is a feature matrix.

In some embodiments, the score is a first score, the method further comprising: in a second pipeline corresponding to a second care provision type: constructing, based on the second care provision type, a third data structure based on healthcare claims data of the plurality of healthcare providers; calculating, based on the third data structure, a second score for the particular provider of the plurality of providers, wherein the score is indicative of an amount of deviation by the particular provider from the one or more common patterns when providing the second care provision type; calculating an overall score for the particular provider based on the first score and the second score; and causing display of the particular provider based on the overall score.

In some embodiments, the method further comprises: automatically ranking the plurality of providers.

In some embodiments, the first care provision type comprises: delivering services, referring services, scheduling services, or sourcing patients to locations.

In some embodiments, the method further comprises: obtaining, based on the second data structure, one or more anomalous features corresponding to the particular provider; receiving data corresponding to a healthcare claim by the particular provider; comparing the one or more anomalous features with the healthcare claim; and flagging the healthcare claim if there is an overlap between the healthcare claim and the one or more anomalous features.

An exemplary electronic device comprises: one or more processors; a memory; and one or more programs, wherein the one or more programs are stored in the memory and configured to be executed by the one or more processors, the one or more programs including instructions for: in a first pipeline corresponding to a first care provision type: constructing, based on the first care provision type, a first data structure based on medical claims data of a plurality of healthcare providers; automatically performing factorization on the first data structure to obtain a set of data structures, wherein the set of data structures is indicative one or more common patterns among the plurality of healthcare providers; automatically, based on the set of data structures, obtaining a second data structure, wherein the second data structure is indicative of deviation by the plurality of healthcare providers from the one or more common patterns; calculating, based on the second data structure, a score for a particular provider of the plurality of providers, wherein the score is indicative of an amount of deviation of the particular provider from the one or more common patterns when providing the first care provision type; causing display of the particular provider based on the score.

An exemplary non-transitory computer-readable storage medium storing one or more programs, the one or more programs comprising instructions, which when executed by one or more processors of an electronic device having a display, cause the electronic device to: in a first pipeline corresponding to a first care provision type: constructing, based on the first care provision type, a first data structure based on medical claims data of a plurality of healthcare providers; automatically performing factorization on the first data structure to obtain a set of data structures, wherein the set of data structures is indicative one or more common patterns among the plurality of healthcare providers; automatically, based on the set of data structures, obtaining a second data structure, wherein the second data structure is indicative of deviation by the plurality of healthcare providers from the one or more common patterns; calculating, based on the second data structure, a score for a particular provider of the plurality of providers, wherein the score is indicative of an amount of deviation of the particular provider from the one or more common patterns when providing the first care provision type; causing display of the particular provider based on the score.

An exemplary computer-implemented method for automatically detecting anomalous healthcare providers and anomalous healthcare claims comprises: in a first pipeline corresponding to a first set of care provision characteristics: constructing, based on the first set of care provision characteristics, a first data structure based on healthcare claims data of a plurality of healthcare providers; automatically performing factorization on the first data structure to obtain a set of data structures, wherein the set of data structures is indicative of the one or more common patterns among the plurality of healthcare providers; automatically, based on the set of data structures, obtaining a second data structure, wherein the second data structure is indicative of deviations by the plurality of healthcare providers from the one or more common patterns; calculating, based on the second data structure, a score for a particular provider of the plurality of providers or a particular healthcare claim of a plurality of healthcare claims, wherein the score is indicative of an amount of deviation of the particular provider or the particular claim from the one or more common patterns when providing the first care provision type; causing a set of actions to be executed based on the score.

In some embodiments, the care provision characteristics include diagnostic information, procedural information, setting information, scheduling information, referral information, location information, ownership information and combinations thereof.

In some embodiments, the first data structure comprises a tensor.

In some embodiments, the tensor comprises a multi-dimensional array, wherein each cell is an exact or normalized count for each provider or for a combination of providers of the occurrence of a specific combination of care provision characteristics.

In some embodiments, the set of data structures comprises a set of rank-1 tensors.

In some embodiments, the factorization is a CANDECOMP/PARAFAC (CP) or a Tucker tensor factorization.

In some embodiments, the second data structure comprises a reconstruction error tensor.

In some embodiments, the method further comprises: identifying an array of the reconstruction error tensor, wherein the array corresponds to the particular provider; and calculating the score for the particular provider based on the array; and calculating scores of features or their co-occurrence with other features based on the array.

In some embodiments, the score is a maximum value of the array, an average of the array, a sum of the array, a sum of the absolute values of the array, a sum of either of the positive or the absolute values of the negative values of the array, a sum of the output of a function over each value of the array, wherein the function is configured to receive the corresponding error values for all providers and compute deviations from one-dimensional summary statistics or order statistics.

In some embodiments, the set of data structures comprise an autoencoder.

In some embodiments, the second data structure comprises a reconstruction error matrix.

In some embodiments, the autoencoder is a robust deep autoencoder.

In some embodiments, the method further comprises: identifying a vector of the reconstruction error matrix, wherein the vector corresponds to the particular provider; and calculating the score for the particular provider based on the vector, and calculating scores of features based on the vector.

In some embodiments, the first data structure comprises a feature matrix.

In some embodiments, the factorization is implemented based on singular value decomposition, principal component analysis or non-negative factorization.

In some embodiments, the second data structure comprises a reconstruction error matrix.

In some embodiments, the method further comprises: identifying a vector of the reconstruction error matrix, wherein the vector corresponds to the particular provider; and calculating the score for the particular provider based on the vector, and calculating the scores of features based on the vector.

In some embodiments, the method further comprises: receiving a user input indicative of a specialty, wherein the plurality of providers is selected based on the specialty.

In some embodiments, the method further comprises: receiving a user input indicative of a geography, wherein the plurality of providers is selected based on the geography.

In some embodiments, the method further comprises: receiving a user input indicative of a line of business, such as Medicare, Medicaid, Commercial, Family, Individual or Employer health insurance, wherein the plurality of providers is selected based on the line of business.

In some embodiments, the score is a first score, the method further comprising: in a second pipeline corresponding to a second set of care provision characteristics: constructing, based on the second set of care provision characteristics, a third data structure based on healthcare claims data of the plurality of healthcare providers; calculating, based on the third data structure, a second score for the particular provider of the plurality of providers or the particular healthcare claim of a plurality of healthcare claims, wherein the score is indicative of an amount of deviation by the particular provider or the particular claim from the one or more common patterns when providing the second care provision type; calculating an overall score for the particular provider or the particular claim based on the first score and the second score; and causing a set of actions to be executed based on the overall score.

In some embodiments, the set of actions to be executed include pre-pay or post-pay claims, eligibility, authorization and documentation processing and adjudication, special investigation and recovery.

In some embodiments, suspicious providers or claims result in claims denial, claims hold or claims documentation request.

In some embodiments, claims denial, claims hold or claims documentation request may be implemented for either all claims for a suspicious provider or a plurality of claims meeting suspicious features for a suspicious provider.

In some embodiments, the set of actions to be executed include the generation of a ranking of the plurality of providers or healthcare claims and generation of a list of providers or healthcare claims that are flagged as suspicious.

In some embodiments, the set of actions to be executed include the generation of a list of the suspiciousness scores for the plurality of providers or healthcare claims and features of suspicious activity for each provider.

In some embodiments, the method further comprises: display of the actions to be executed.

In some embodiments, the method further comprises: making the actions to be executed available through an application programmatic interface.

In some embodiments, factorization is performed using graph-based features.

An exemplary computer-implemented method for automatically detecting anomalous healthcare providers and anomalous healthcare claims, comprises: in a first pipeline corresponding to a first set of care provision characteristics: constructing, based on the first set of care provision characteristics, a first data structure based on healthcare claims data of a plurality of healthcare providers; automatically performing anomaly detection on the first data structure to obtain a set of data structures, wherein the set of data structures is indicative of one or more common patterns among the plurality of healthcare providers; automatically, based on the set of data structures, obtaining a second data structure, wherein the second data structure is indicative of deviations by the plurality of healthcare providers from the one or more common patterns; calculating, based on the second data structure, a score for a particular provider of the plurality of providers or a particular healthcare claim of a plurality of healthcare claims, wherein the score is indicative of an amount of deviation of the particular provider or the particular claim from the one or more common patterns when providing the first care provision type; causing a set of actions to be executed based on the score.

In some embodiments, anomaly detection is performed using a one-class support vector machine, support vector data description, isolation forest, nearest-neighbor based techniques, histogram-based techniques and attribute-wise learning for scoring outliers.

In some embodiments, anomaly detection is performed using graph-based features.

In some embodiments, anomaly detection is performed using a rule-based engine.

In some embodiments, the care provision characteristics include diagnostic information, procedural information, setting information, scheduling information, referral information, location information, ownership information and combinations thereof.

In some embodiments, the method further comprises: receiving a user input indicative of a specialty, wherein the plurality of providers is selected based on the specialty.

In some embodiments, the method further comprises: receiving a user input indicative of a geography, wherein the plurality of providers is selected based on the geography.

In some embodiments, the method further comprises: receiving a user input indicative of a line of business, such as Medicare, Medicaid, Commercial, Family, Individual or Employer health insurance, wherein the plurality of providers is selected based on the line of business.

In some embodiments, the score is a first score, and the method further comprises: in a second pipeline corresponding to a second set of care provision characteristics: constructing, based on the second set of care provision characteristics, a third data structure based on healthcare claims data of the plurality of healthcare providers; calculating, based on the third data structure, a second score for the particular provider of the plurality of providers or the particular healthcare claim of a plurality of healthcare claims, wherein the score is indicative of an amount of deviation by the particular provider or the particular claim from the most common patterns when providing the second care provision type; calculating an overall score for the particular provider or the particular claim based on the first score and the second score; and causing a set of actions to be executed based on the overall score.

In some embodiments, the set of actions to be executed include pre-pay or post-pay claims, eligibility, authorization and documentation processing and adjudication, special investigation and recovery.

In some embodiments, suspicious providers or claims result in claims denial, claims hold or claims documentation request.

In some embodiments, claims denial, claims hold or claims documentation request may be implemented for either all claims for a suspicious provider or a plurality of claims meeting suspicious features for a suspicious provider.

In some embodiments, the set of actions to be executed include the generation of a ranking of the plurality of providers or healthcare claims and generation of a list of providers or healthcare claims that are flagged as suspicious.

In some embodiments, the set of actions to be executed include the generation of a list of the suspiciousness scores for the plurality of providers or healthcare claims and features of suspicious activity for each provider.

An exemplary electronic device comprises: one or more processors; a memory; and one or more programs, wherein the one or more programs are stored in the memory and configured to be executed by the one or more processors, the one or more programs including instructions for: in a first pipeline corresponding to a first set of care provision characteristics: constructing, based on the first set of care provision characteristics, a first data structure based on healthcare claims data of a plurality of healthcare providers; automatically performing factorization on the first data structure to obtain a set of data structures, wherein the set of data structures is indicative of the one or more common patterns among the plurality of healthcare providers; automatically, based on the set of data structures, obtaining a second data structure, wherein the second data structure is indicative of deviations by the plurality of healthcare providers from the one or more common patterns; calculating, based on the second data structure, a score for a particular provider of the plurality of providers or a particular healthcare claim of a plurality of healthcare claims, wherein the score is indicative of an amount of deviation of the particular provider or the particular claim from the one or more common patterns when providing the first care provision type; causing a set of actions to be executed based on the score.

An non-transitory computer-readable storage medium stores one or more programs, the one or more programs comprising instructions, which when executed by one or more processors of an electronic device, cause the electronic device to in a first pipeline corresponding to a first set of care provision characteristics: constructing, based on the first set of care provision characteristics, a first data structure based on healthcare claims data of a plurality of healthcare providers; automatically performing factorization on the first data structure to obtain a set of data structures, wherein the set of data structures is indicative of the one or more common patterns among the plurality of healthcare providers; automatically, based on the set of data structures, obtaining a second data structure, wherein the second data structure is indicative of deviations by the plurality of healthcare providers from the one or more common patterns; calculating, based on the second data structure, a score for a particular provider of the plurality of providers or a particular healthcare claim of a plurality of healthcare claims, wherein the score is indicative of an amount of deviation of the particular provider or the particular claim from the one or more common patterns when providing the first care provision type; causing a set of actions to be executed based on the score.

An electronic device comprises one or more processors; a memory; and one or more programs, wherein the one or more programs are stored in the memory and configured to be executed by the one or more processors, the one or more programs including instructions for: in a first pipeline corresponding to a first set of care provision characteristics: constructing, based on the first set of care provision characteristics, a first data structure based on healthcare claims data of a plurality of healthcare providers; automatically performing anomaly detection on the first data structure to obtain a set of data structures, wherein the set of data structures is indicative of one or more common patterns among the plurality of healthcare providers; automatically, based on the set of data structures, obtaining a second data structure, wherein the second data structure is indicative of deviations by the plurality of healthcare providers from the one or more common patterns; calculating, based on the second data structure, a score for a particular provider of the plurality of providers or a particular healthcare claim of a plurality of healthcare claims, wherein the score is indicative of an amount of deviation of the particular provider or the particular claim from the one or more common patterns when providing the first care provision type; causing a set of actions to be executed based on the score.

A non-transitory computer-readable storage medium stores one or more programs, the one or more programs comprising instructions, which when executed by one or more processors of an electronic device, cause the electronic device to: in a first pipeline corresponding to a first set of care provision characteristics: constructing, based on the first set of care provision characteristics, a first data structure based on healthcare claims data of a plurality of healthcare providers; automatically performing anomaly detection on the first data structure to obtain a set of data structures, wherein the set of data structures is indicative of one or more common patterns among the plurality of healthcare providers; automatically, based on the set of data structures, obtaining a second data structure, wherein the second data structure is indicative of deviations by the plurality of healthcare providers from the one or more common patterns; calculating, based on the second data structure, a score for a particular provider of the plurality of providers or a particular healthcare claim of a plurality of healthcare claims, wherein the score is indicative of an amount of deviation of the particular provider or the particular claim from the one or more common patterns when providing the first care provision type; causing a set of actions to be executed based on the score.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4A illustrates an exemplary feature matrix, in accordance with some embodiments.

DETAILED DESCRIPTION

Figure 1A:
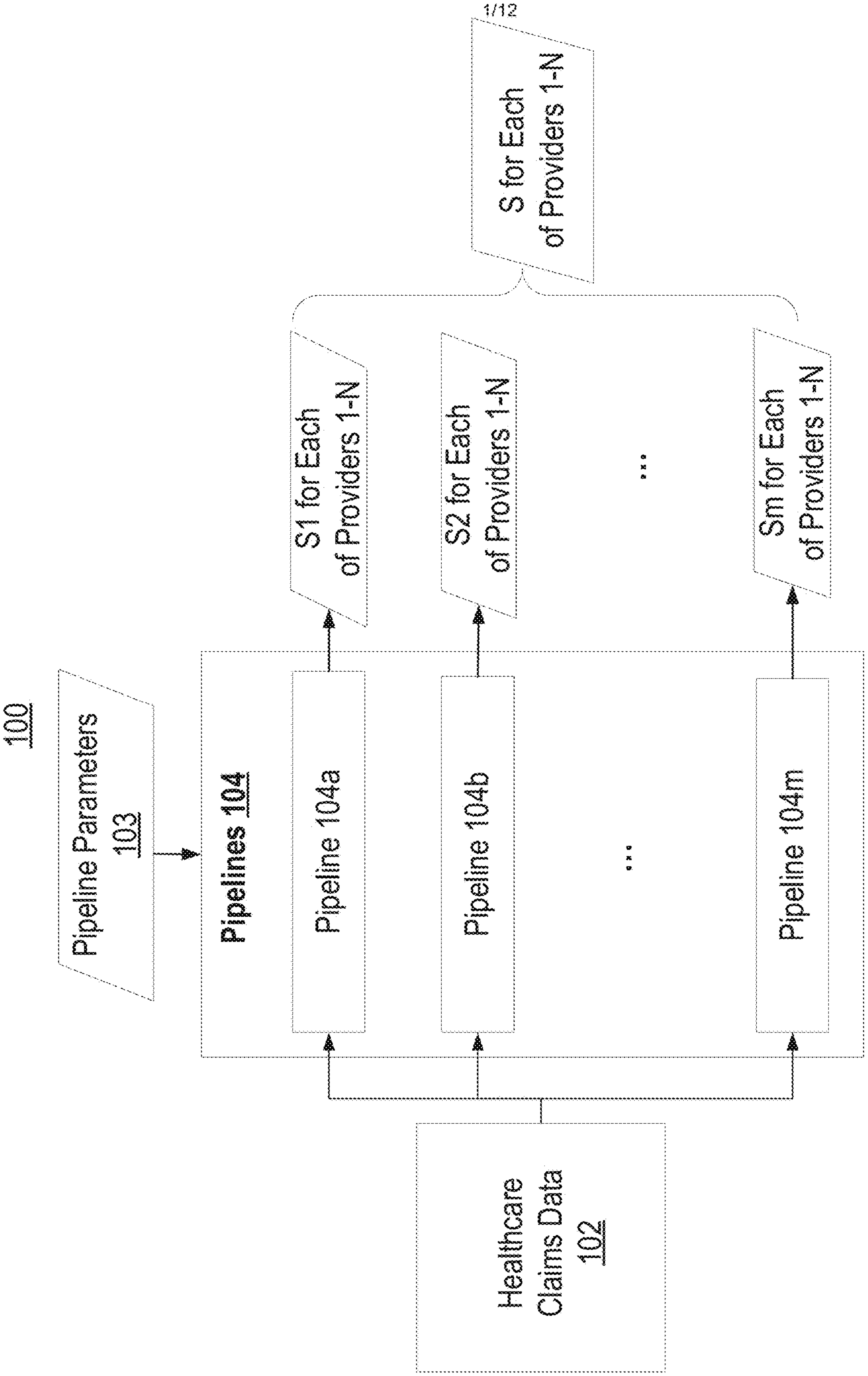
FIG. 1A illustrates an exemplary system for identifying fraud and abuse (e.g., waste) in healthcare providers, in accordance with some embodiments.

The present disclosure is directed to methods, systems, electronic devices, apparatus, and non-transitory storage media for identifying abnormal behavior (e.g., by healthcare providers). An exemplary system can determine a score of suspiciousness (or suspiciousness score) for a healthcare provider, which reflects the extent to which the provider's overall care provision patterns (e.g., patterns of diagnoses, procedures, settings, referrals, scheduling, sourcing patients to locations) deviate from normal or common patterns, which may indicate fraud or abuse. Based on the suspicious scores, the system can rank healthcare providers and identify the most suspicious providers.

In some embodiments, unsupervised machine-learning techniques can be used to learn the most common patterns of each type of care provision (e.g., the most common patterns for diagnoses and procedures, the most common patterns for care settings, the most common patterns for referrals, the most common patterns for scheduling, the most common patterns for sourcing patients to locations) for a given specialty. An individual healthcare provider's suspiciousness score is computed to capture how much their care provision patterns deviate from the most normal or common ones within their specialty; such a deviation may be indicative of fraud or abuse. The providers can be ranked or grouped using their corresponding suspiciousness scores.

Embodiments of the present disclosure can be deployed in one or more client devices, one or more server devices, or a combination thereof. In some embodiments, the system comprises a software application or service accessible by relevant personnel (e.g., an auditor, a reviewer) on electronic devices. In some embodiments, the system comprises one or more application programming interfaces ("API") that allow integration of the system with existing platforms (e.g., alert systems; pre-pay claims, eligibility, authorization and documentation processing and adjudication systems; post-pay special investigation and recovery systems etc.) and databases.

In some embodiments, the system can provide one or more user interfaces for: receiving one or more inputs for calculating a suspiciousness score (e.g., specifying a specialty, a time, a provider), displaying suspiciousness scores of healthcare providers, displaying features through which patterns of FA are reflected, organizing suspiciousness scores (e.g., sorting, filtering), and making recommendations about healthcare providers and claims, eligibility, authorization and documentation (e.g., investigate providers, deny claims, hold claims etc.).

In general, the suspiciousness scores can be used to flag suspicious providers. This can occur pre-payment and/or post-payment, as described below.

In some embodiments, the suspiciousness scores can be used for pre-pay filtering of claims and investigation of providers. For example, the system can automatically reject claims before they are paid out and/or automatically request more supporting evidence before claims are paid (e.g., if the provider has a suspiciousness score higher than a predefined threshold). Thus, the suspiciousness scores can be used to prevent inappropriate payment from being made.

In some embodiments, the suspiciousness scores can be used for post-pay recovery of payments and investigation of providers. For example, the system can identify potentially FA providers (e.g., if the suspiciousness scores are higher than a predefined threshold) who have received payments in the past and FA claims that might have been paid out in the past. Thus, the suspiciousness scores can be used to initiate investigation and disciplinary action and recover payments that may have been inappropriately made in the past.

In some embodiments, the system can automatically identify a set of providers whose suspiciousness scores are above a certain threshold. This way, the system can triage and prioritize highly suspicious provider instances for manual expert review or investigation. In some embodiments, the system can automatically exclude the set of providers from a database (e.g., in-network benefits).

In addition to identifying the most suspicious providers, the system can identify the specific pattern of fraud each provider is committing. For example, the system produces, for each provider, a suspiciousness score and one or more patterns of fraud associated with that specific provider. The patterns are represented by the specific features (e.g., specific kinds of diagnoses, procedures, locations, settings, referrals, scheduling etc. and combinations thereof) that contribute the most to the provider's suspiciousness score.

The identified patterns of fraud for each provider can be utilized in multiple ways, including for example, in terms of evaluating a provider's observed practice patterns for FA (e.g., by inspecting only the subset of features which are flagged as the most anomalous for changes in these features representative of FA) as well as serving as prior knowledge in a real-time health insurance FA claim flagging systems. For example, the system can automatically deny only the "bad" claims from a potentially fraudulent provider. This may, for example, be appropriate where it is desirable that legitimate claims for providers who commit fraud not be impacted and action should only be focused around claims that are known to be meeting fraudulent patterns characteristic of the provider.

In some embodiments, the system obtains a nested data collection of the following form:

<suspicious provider p_1, [list of anomalous features per provider p_1],

. . . , suspicious provider p_N, [list of anomalous features per provider p_N]>

The above data collection contains a list of suspicious providers as well as a list of the features observed to be anomalous for each provider based on their care provision patterns.

Then, for each incoming claim, the providers within the claim (e.g., delivering, referring) are tested for inclusion in the above nested data collection, which can be efficiently done in real-time with O(1) amortized computational cost per provider look-up since the above data collection can be implemented via a hash table. If the provider has been deemed suspicious based on the system's output and the features observed for the incoming claim (e.g., certain diagnoses, procedures, locations, settings, referrals, scheduling or combination thereof) overlap with the ones indicated as anomalous by the system, the claim is flagged for potential action.

In some embodiments, the overlap can be the presence of these features (i.e., the presence of the diagnoses, procedures, locations, settings, referrals, scheduling or combination thereof) and the flagging process is to check for the occurrence of these features. In other embodiments, the overlap can be the presence of these features along with threshold values and the flagging process is to check for these features being above these threshold values. In still other embodiments, the overlap can be functions that take as input these features and the flagging process can be to apply these functions to the features and use the outputs of these functions to flag claims. These embodiments are presented as only a few examples of the ways in which features can be used to flag claims. Additional rules can be employed to further constrain the claim's action based on external knowledge depending on the particular embodiment (e.g., prior history of sanctioning, certification). The system can be scheduled to periodically re-run (e.g., daily, weekly, monthly) so as to maintain an up-to-date state of knowledge about suspicious providers and anomalous features.

In some embodiments, the system can provide visualizations of healthcare providers based on calculated suspiciousness scores. For example, the system can allow a user to view the top suspicious healthcare providers by geographic regions, specialties, lines of business (e.g., Medicare, Medicaid, Commercial, Family, Individual, Employer health plans). Also, the system can allow the user to observe the percentage of each provider's revenue considered to be acquired by suspicious claims (e.g., those claims matching certain pre-specified criteria, such as the existence of certain features), as well as to refine the set of suspicious providers based on several criteria such as a certain minimum percentage of suspicious acquired revenue (as a fraction of a provider's total revenue). As another example, the system can allow a user to view how a provider's suspiciousness scores have evolved over time. In some embodiments, the system can allow the user to utilize an API to retrieve and inspect individual claims of suspicious providers (e.g., claims where a certain feature is present) so as to support post-pay recovery and investigation. In some embodiments where pre-pay filtering of suspicious claims is one of the target use cases, the system may provide recommendations to either reject a claim or issue an inquiry to the claim's delivering provider asking for additional documentation around the claim's validity or medical necessity.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of the present disclosure are advantageous in multiple aspects.

A) Feasibility regarding the input data elements: The care provision attributes used by embodiments of the present invention include essential components of a health insurance claim filing system. For example, billing for a claim with empty diagnosis and procedure codes would likely be rejected by an insurance company as lacking substantial documentation.

Similarly, there are certain types of health maintenance organization (HMO) plans where a referral from a primary care provider (PCP) is necessary for a specialist visit or a special test to get reimbursed. Information about the dates of claims are also essential, providing information about scheduling. Finally, the location of the members and providers are also well established by healthcare organizations.

B) Coverage of different fraud or abuse schemes: Flagging providers with anomalous patterns of care provision (for example, affecting diagnoses, procedures, locations, settings, referrals, scheduling etc. and combinations thereof) offers a unified approach that can cover and detect many different classes of FA, such as systematically billing for medically unnecessary procedures, falsifying diagnoses to justify billing, and participating in illegal referral schemes also known as kickbacks.

C) No input labels of FA are necessary: Some embodiments of the present disclosure are based on unsupervised machine learning, thus no manually-crafted annotations of what constitutes FA are needed as input. Supervised learning techniques applied to FA detection can be fundamentally limited by the extreme scarcity of publicly-available labels of FA and their ability to only discover examples of FA that are already known and therefore labeled in data available for supervised learning.

D) Actionable outputs are provided: In some embodiments, prioritization of provider instances for manual expert review can be achieved by simply sorting providers in descending order of their suspiciousness scores. In other embodiments, this prioritization can be achieved by sorting claims based on the suspiciousness scores of providers and/or claims. Given the limited capacity of teams conducting FA investigations, such a prioritization of providers or claims is of critical importance. Additionally, the embodiments of the present invention examine the overall suspiciousness of a provider's care provision practices, which encapsulates their performance over a period of time rather than a single aberration, and is better tailored towards justifying systematic FA, which is not thrown off by a single aberration that may be due to non-FA data entry errors or noise. Provider-centered corrective actions which are informed by embodiments of the present disclosure (e.g., exclusion of a flagged provider from in-network benefits, denial of claims of a certain type) may result in significant impact with respect to both mitigating patient harm and reducing healthcare costs. Specific ways in which the system might lead to positive impact include but are not limited to: a) expert review, informed by the system's output, may lead to the conclusion that most of a provider's practice is fraudulent, thus potentially leading to revoking the provider's privileges, in which case future provider's claims would not occur; b) claim denial, informed by the system's output, might lead to change in the corresponding provider's behavior (e.g., lowering the rates of or abandoning a fraudulent scheme altogether); c) either one of revoking a fraudulent provider's privileges or denying one or more of their claims may incur change in behavior of providers who are connected to the one facing the direct consequences of their fraudulent activity. For example, in the case of an orchestrated illegal kickback scheme involving multiple providers, a revoked provider involved might inform others in the coordinated scheme, potentially leading to multiple fraudulent providers reducing the rates of their fraudulent activities.

Providers within a given specialty often demonstrate similar patterns in their healthcare encounters and transactions. As examples:

a) There are characteristic patterns of procedures and diagnoses that frequently co-occur in claims billed by providers of the given specialty (e.g., angioplasty and stenting are among the most common procedures an interventional cardiologist would bill for patients with atherosclerosis).
b) There are characteristic patterns of referrals (e.g., a cardiologist may refer patients with chest pain on exertion to a lab for a stress test).
c) There are characteristic settings of care (e.g., a cardiologist may perform coronary artery bypass grafts in an inpatient setting).

d) There are characteristic patterns of scheduling (e.g., a cardiologist may set up six month evaluation and management visits with patients with congestive heart failure).

e) There are characteristic patterns of location (e.g., a cardiologist in a metro area may have a specific patient catchment area served).

The above-referenced examples are merely illustrative, as embodiments of the present disclosure are not limited to these specific patterns of care provision attributes and can be readily extended to other attributes for which there is general consistency for providers in a given specialty.

Thus, when an individual provider's care provision attributes substantially deviate from those of their peers (e.g., same specialty, practice, region and/or other notions of a peer), the provider may be potentially performing anomalously and may thus be a candidate for committing FA. For example, in the case of a referring provider, substantial deviation from the specialty's most commonly referred types of procedures (and associated diagnoses) may be indicative of an underlying financial incentive driving such referral behavior (e.g., illegal kickback). An example of such deviation may arise if the vast majority of an interventional cardiologist's referrals correspond to genetic testing procedures, while those tests would rarely be billed in claims where other interventional cardiologists would be the referring providers.

FIG. 1A depicts an exemplary system 100 for identifying fraud and abuse in healthcare providers, in accordance with some embodiments. System 100 comprises multiple pipelines that may operate in parallel simultaneously, with each pipeline corresponding to a certain type of care provision (e.g., attending/rendering services, referring services, scheduling services, sourcing patients). In the depicted examples, the system comprises:

a) a pipeline 104*a* for detecting anomalous providers attending/rendering diagnostic and procedural services;

b) a pipeline 104*b* for detecting anomalous providers referring services;

c) a pipeline 104*c* for detecting anomalous providers scheduling services;

d) . . .

e) a pipeline 104*n* for detecting anomalous providers sourcing patients from locations.

With reference to FIG. 1A, each of the pipelines is configured to receive data (e.g., healthcare claims data) 102 of multiple providers, identify one or more of the most common patterns among the multiple peer providers 1-N, and output a score for each of providers 1-N reflecting the deviation of his or her care provision pattern from the most common patterns among the provider's peers. Further, pipeline parameters 103 can be provided (e.g., by a user) to specify the properties of the pipelines. The pipeline parameters 103 can specify a specialty, a time period, a geographical region, or any combination thereof. For example, if the pipeline parameters 103 specify cardiology, January-June 2020, and the United States, the pipeline 104*a* can extract from the data 102 healthcare claims data for which the delivering provider is a cardiologist, the time period is January-June 2020, and the location is the United States. The extracted data can then be used as training data for the pipeline 104*a* to identify the most common patterns capturing the variation of services delivered among cardiologists in the United States during January-June 2020.

Thus, subject to the pipeline parameters (e.g., within a specific specialty), pipelines 104*a*-104*m* can identify the following:

a) 104*a*: identifying the most common patterns among providers 1-N for attending/rendering diagnostic and procedural services;

b) 104*b*: identifying the most common patterns among providers 1-N for referring services;

c) 104*c*: identifying the most common patterns among providers 1-N for scheduling services;

d) . . .

e) 104*n*: identifying the most common patterns among providers 1-N for sourcing patients from locations.

Further, each of pipelines 104*a*-104*m* can, for each provider, determine the provider's deviation from the most common patterns corresponding to each pipeline:

a) 104*a*: calculating, for each of providers 1-N, a score $S_1$ indicating how much the provider deviates from the most common patterns for attending/rendering diagnostic and procedural services;

b) 104*b*: calculating, for each of providers 1-N, a score $S_2$ indicating how much the provider deviates from the most common patterns for referring services;

c) 104*c*: calculating, for each of providers 1-N, a score $S_3$ indicating how much the provider deviates from the most common patterns for scheduling services;

d) . . .

e) 104*n*: calculating, for each of providers 1-N, a score $S_m$ indicating how much the provider deviates from the most common patterns for sourcing patients from locations.

Thus, for each provider, a plurality of scores $S_1$-$S_m$ are obtained. In some embodiments, a single overall score S can be obtained for a provider. In some embodiments, the maximum of the provider's scores is retrieved and returned as his or her overall suspiciousness score. In other embodiments, the provider's scores can be combined to calculate the overall suspiciousness score (e.g., taking the average, thresholding the scores, defining rules based on the scores, or by using these scores as inputs to one or more models, etc.). For example, to threshold the scores, the system can extract a binary indicator for each pipeline to assess whether the corresponding $S_i$ score exceeds 0.9 (in case that the system has normalized the individual scores to the [0, 1] range). Then the system can perform a transformation over those binary indicators (e.g., max/average, etc.).

It should be appreciated that the system of FIG. 1A is merely exemplary. While the system 100 provides a dedicated pipeline for each type of care provision and includes multiple parallel pipelines, some or all of pipelines 104*a*-104*m* can be combined into a single pipeline. Further, while system 100 includes pipelines corresponding to diagnoses, procedures, settings, referrals, scheduling, and location, pipelines corresponding to other types of care provision can be included (as well as combinations and subsets thereof).

Figure 1B:
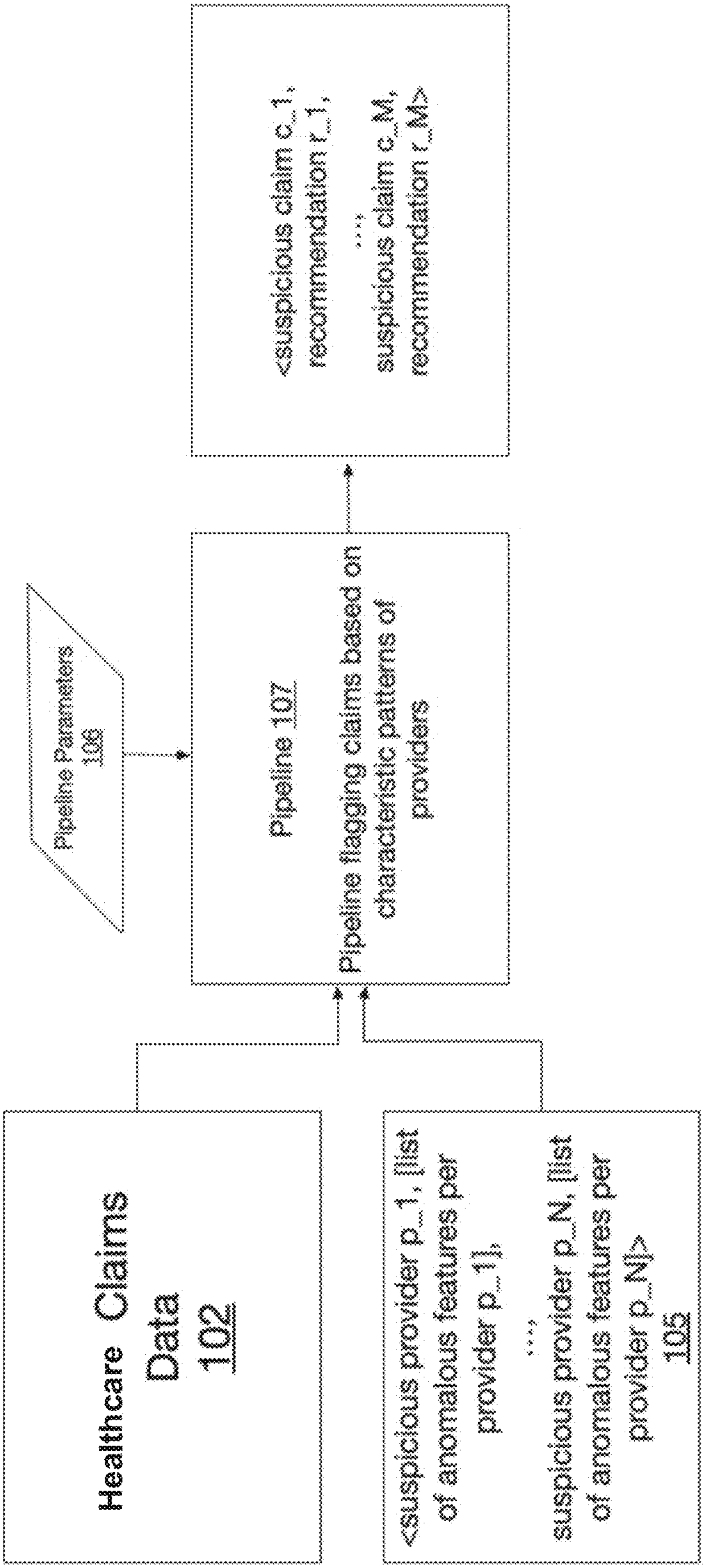
FIG. 1B depicts an exemplary process for flagging claims based on characteristic patterns of providers deemed suspicious.

FIG. 1B depicts an exemplary process for flagging claims based on characteristic patterns of providers deemed suspicious, according to some embodiments. The input elements of the pipeline flagging claims are: i) healthcare claims data (102); ii) a data structure (105) containing identifiers of providers deemed suspicious and for each one of the providers a list of features considered to be anomalous with respect to each particular provider; iii) parameters (106) reflecting the characteristic patterns of providers based on which claims will be flagged. In some embodiments, the data structure 105 will contain information about the providers extracted through the exemplary system 100, potentially using a threshold on the overall suspiciousness score of every provider to determine whether the provider would be included in the data structure 105. In some embodiments, the anomalous features per provider would be extracted through the exemplary system 100, by inspecting how a provider's overall suspiciousness score can be attributed to individual feature value deviations from the model estimates. An example of such an anomalous feature might be the overutilization of a certain procedure in claims with a particular principal diagnosis; a relevant example of how such information might be extracted is provided below.

Both the set of suspicious providers and the list of anomalous features per provider can be augmented through external knowledge and would not be strictly restricted to the input provided as the output of the exemplary system 100. For example, knowledge from a different health insurance plan may be transferred (if such knowledge might be available) indicating certain providers as suspicious and certain features observed on a different health plan as anomalous. The parameters 106 contain the various specifications upon which incoming claims will be flagged, given the data structure 105 and the healthcare claims to be inspected. The specifications might vary across different types of claims, different types of providers, or even across different individual providers, in order to provide the investigator/user with enough flexibility to specify ways in which claims will be flagged.

In order to illustrate this capability, a few examples are provided below, but the present disclosure is not limited to them:

i) flag claims of a delivering provider p_i, where p_i exists in data structure 105 and any of their anomalous features listed in data structure 105 is observed in an incoming claim (e.g., a certain genetic test is listed as being overutilized by p_i in data structure 105 and the corresponding suspicious provider p_i files a claim including that particular genetic test);

ii) flag a certain type of claims of a suspicious provider based on anomalous rule-based features listed in data structure 105 related to their referral patterns (e.g., flag an incoming claim where the referring provider listed has systematically being referring members he/she has never seen in the past to laboratories and the same pattern is observed in the incoming laboratory claim).

Based on the claims flagged for potential action, the pipeline 107 provides a recommendation for each one of them (e.g., claim rejection, issue an inquiry to the delivering provider for additional information/documentation to substantiate the medical necessity or validity of the claim, etc.). In some embodiments, the recommendations may be based on the suspiciousness score of every provider; for example, the providers with the highest range of suspiciousness scores might have their flagged claims being rejected. In some embodiments, a score can be assigned to every claim to indicate the deviation of that particular claim from the most common patterns. In other embodiments, those recommendations may be based on the percentage of revenue of a provider over a period of time (e.g., last year) being flagged and considered suspicious. In other embodiments, those recommendations may be dependent on the type of claims (e.g., rejecting a particular type of claims where prior history of a provider suggests focused FA); they may also be dependent on whether expert review of a provider's historical claims (after being highly-ranked as suspicious by the system) has validated the provider as being highly suspicious of conducting FA.

In some embodiments, the system causes one or more treatments to be administered to a patient by a provider based on the suspiciousness score of the provider. For example, if the suspiciousness score of the provider is below a threshold, the provider is deemed trustworthy and a treatment plan can be approved and/or automatically administered (e.g., by operating one or more medical devices). On the other hand, if the suspiciousness score of the provider is above the threshold, the provider is deemed not trustworthy and a treatment plan can be rejected and/or interrupted (e.g., by controlling one or more medical devices).

Figure 2A:
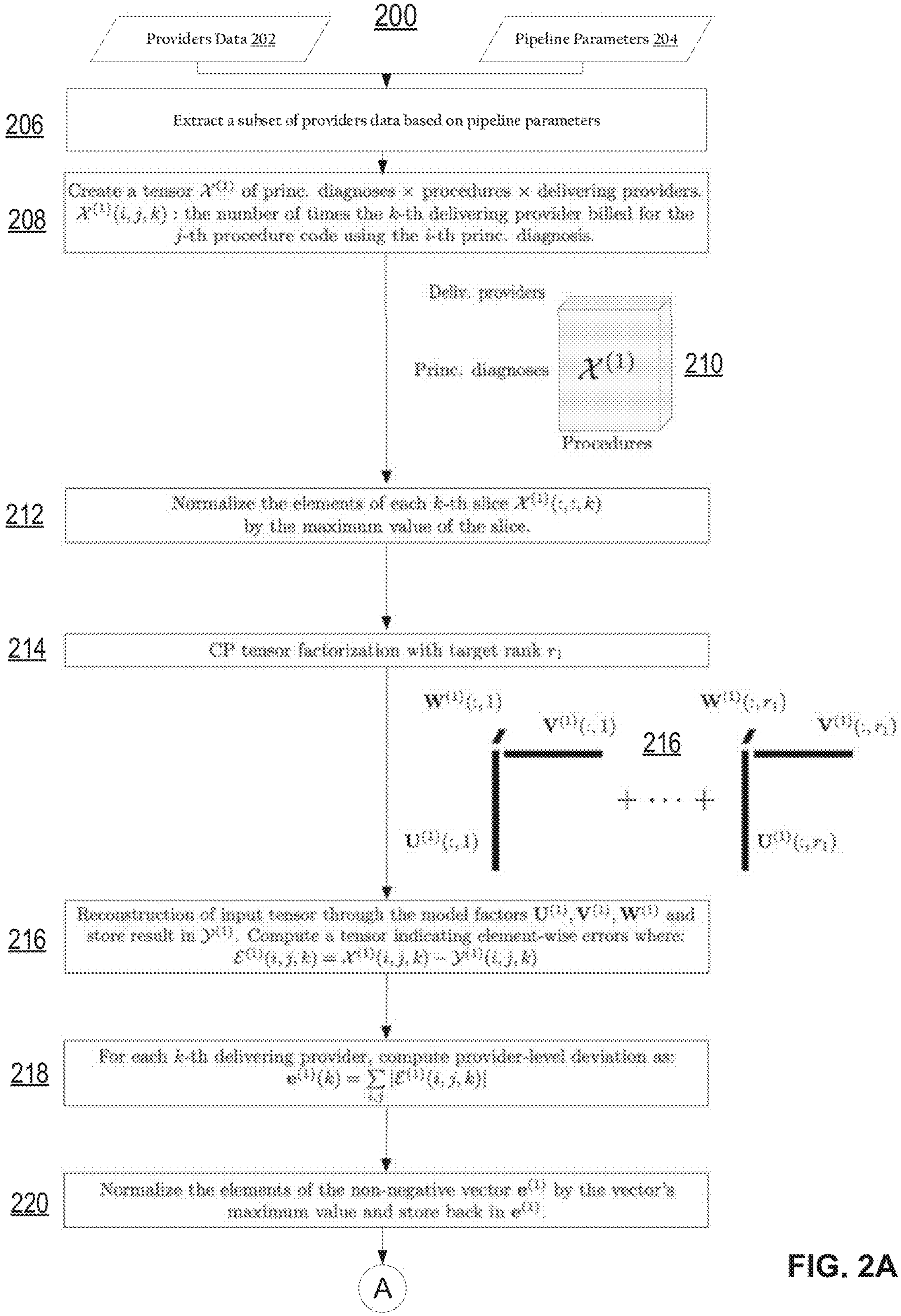
FIG. 2A illustrates an exemplary process for providing a fraud and abuse detection pipeline, in accordance with some embodiments.

FIG. 2A illustrates an exemplary process 200 for providing a fraud and abuse detection pipeline, in accordance with some embodiments. The fraud and abuse detection pipeline can be, for example, pipeline 104*a* of FIG. 1A for detecting anomalous providers attending/rendering (or delivering) diagnostic and procedural services. In FIG. 2, the anomaly detection is performed using dimensionality reduction and, more specifically, using tensor factorization.

With reference to FIG. 2A, an exemplary system (e.g., one or more electronic devices) receives provider data 202 and pipeline parameters 204, as described in detail below.

Figure 2B:
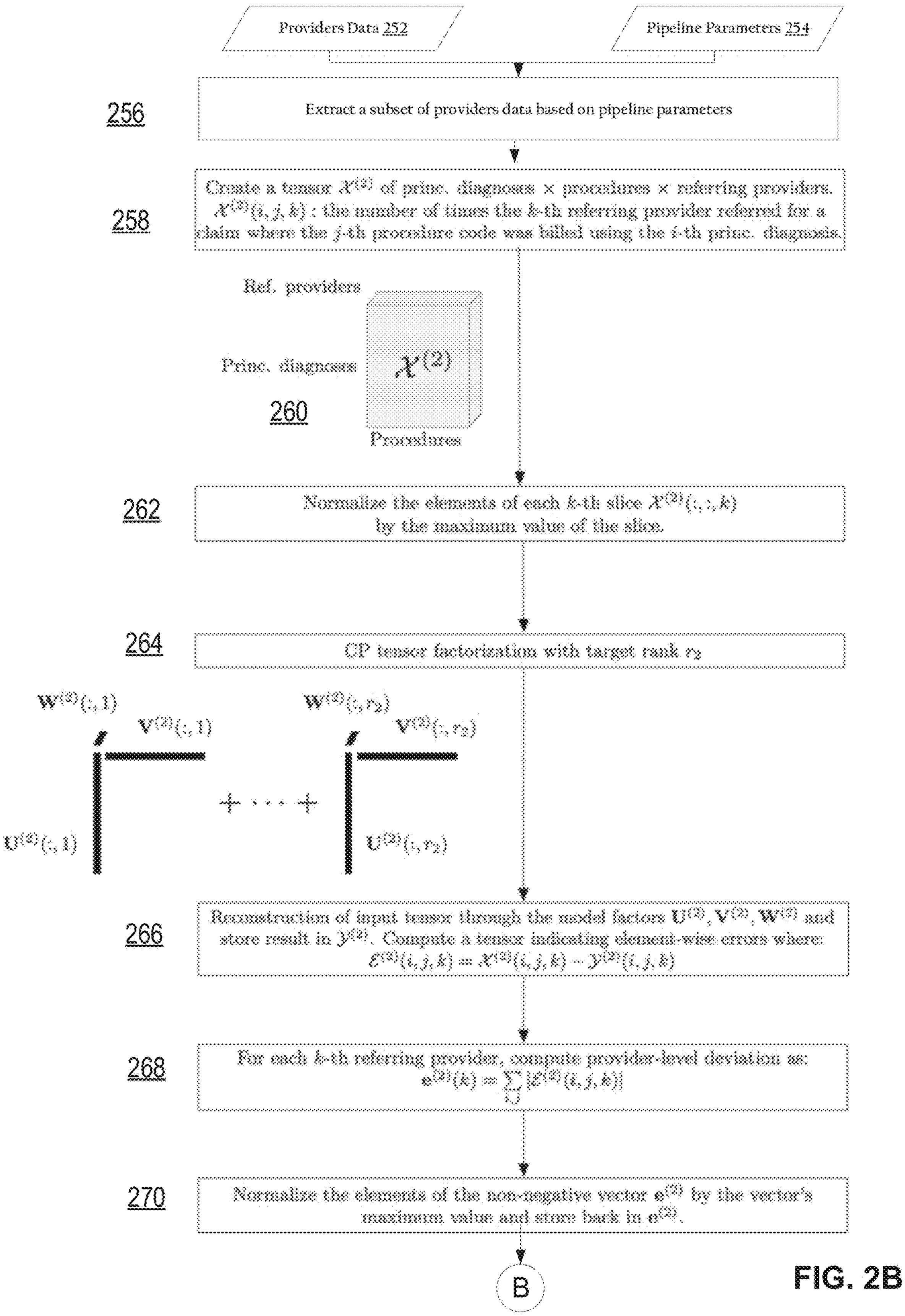
FIG. 2B illustrates an exemplary process for providing a fraud and abuse detection pipeline, in accordance with some embodiments.

The providers data 202 includes healthcare claims data of a plurality of providers. FIG. 2D depicts an exemplary set of providers data 202. As shown, the providers data 202 can include a plurality of healthcare claims and detailed information (e.g., claim ID, claim start date, claim end data, principal diagnosis code, procedure codes, delivering provider ID, delivery provider specialty, referring provider ID, referring provider specialty, etc.) for each claim. Delivering provider refers to the provider attending/rendering the diagnostic and procedural services (i.e., responsible for the care provided).

It should be appreciated that the structure of the providers data 202 in FIG. 2D is merely exemplary. The providers data 202 is not limited to a certain diagnostic or procedure coding scheme (e.g., International Classification of Diseases) or to a certain way of encoding providers (e.g., National Provider Identifier) and their specialties (e.g., Healthcare Provider Taxonomy Code Set). Further, instead of or in addition to including individual instances of diagnoses, procedures, specialties, etc., the providers data 202 can specify categories of each one of those data elements (e.g., grouping sets of procedures into categories of procedures of similar nature). Further, additional data elements may be available in health insurance claims and can be included in providers data 202 depending on the particular embodiment (e.g., location of beneficiary and providers listed on the claim).

The exemplary system further receives pipeline parameters 204. In some embodiments, the pipeline parameters 204 specify a given specialty (e.g., interventional cardiologist) and the start and end dates defining the observation window. In some embodiments, the pipeline parameters 204 further include a target rank $r_1$ for the pipeline in FIG. 2A. The target rank is a non-negative integer defining the size of the computed factorization model. Intuitively, with respect to the particular embodiment described, $r_1$ indicates how many subgroups of procedures and principal diagnoses are utilized to explain the variation of the providers' billing patterns. In some embodiments, an appropriate value of the target rank can be selected to favor reproducible solutions, which would be independent of the random initialization used. Given a certain target rank $r_1$, the reproducibility of a single factor matrix of the solution (e.g., $V^{(1)}$ at the bottom part of FIG. 3C), can be assessed for a pair of different solutions with different initializations (e.g., $V^{(1)}_1$ and $V^{(1)}_2$) by computing correlation coefficients among all pairs of columns of solutions found with different initializations (e.g., pairing each possible column of $V^{(1)}_1$ with each possible column of $V^{(1)}_2$). Note that computing correlation coefficients across every pair of columns at this stage is a preferred approach because: a) correlation is robust against scaling transformations of a factor matrix (in contrast to simpler distance-based measures); b) every pair of columns has to be taken into account, since the two solutions might essentially represent the same underlying latent factors with a permuted set of columns. Having a matrix C of size $r_1$ X $r_1$, containing the pairwise correlation coefficients among each pair of columns of $V^{(1)}_1$ and $V^{(1)}_2$, the following quantity would reflect the dissimilarity among $V^{(1)}_1$ and $V^{(1)}_2$:

$$\frac{1}{2r_1}\left(2r_1 - \sum_{j=1}^{r_1} \max_{1 \le k \le r_1} C(k, j) - \sum_{k=1}^{r_1} \max_{1 \le j \le r_1} C(k, j)\right)$$

The above quantity is known as the "Amari divergence" or "Amari error" in the literature. Measuring such a dissimilarity among a pair of factor matrices can be readily extended to multiple different initial points (more than 2), by considering the average dissimilarity among all pairs of solutions for the same target rank. The above process can be repeated for a series of increasing target ranks (e.g., 1, 2, . . . , up to a maximum target rank specified by the user) and the target rank with the minimum average dissimilarity can be chosen. Among the various solutions for the same target rank retrieved through different random initializations, we pick the one having the minimum approximation error. Even though other ways of identifying the target rank can be used in other embodiments, the way described above is particularly suitable towards our overall anomaly detection task, where the normal or common patterns learnt have to be robust and reproducible, so that deviations from those patterns can be reliably identified.

At block 206, the system extracts a subset of providers data 202 based on the pipeline parameters 204. For example, the system can extract claims that 1) occurred during the observation window considered and 2) where the delivering provider's specialty is the same as the specialty s given as a pipeline parameter.

Figure 3A:
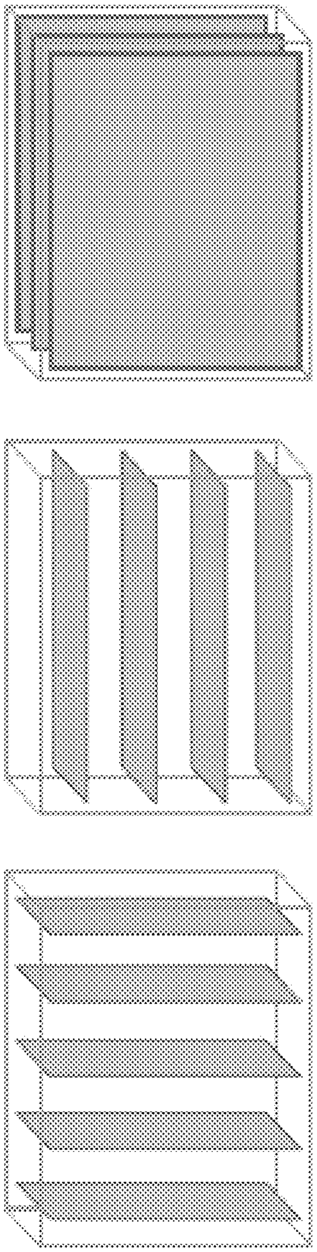
FIG. 3A illustrates slices of an exemplary 3-way tensor, in accordance with some embodiments.

At block 208, the system creates a tensor 210, $X^{(1)}(i, j, k)$, of principal diagnoses X procedures X delivering providers. Tensor 210 is a multidimensional array, where each (i,j,k) cell is the number of times the k-th delivering provider billed for the j-th procedure code using the i-th principal diagnosis. As shown in FIG. 2A, the tensor 210 is a tensor of order 3 (i.e., a 3-way tensor). The 3-way tensor has lateral, horizontal, and frontal subarrays or "slices," as shown in FIG. 3A.

At block 211, the system normalizes the tensor 210. In order to enable meaningful comparisons across the code utilization of different providers-despite the potentially different scales of their co-occurrence counts—the system normalizes the elements of each subarray corresponding to a certain delivering provider (i.e., each principal diagnoses X procedures frontal slice) by dividing the elements with the maximum value of the sub-array. For example, the maximum value is the maximum number of times the provider billed for a procedure using a diagnosis. Other normalization approaches can be used as well, e.g., normalizing by the sum of the provider's co-occurrence counts.

Figure 3B:
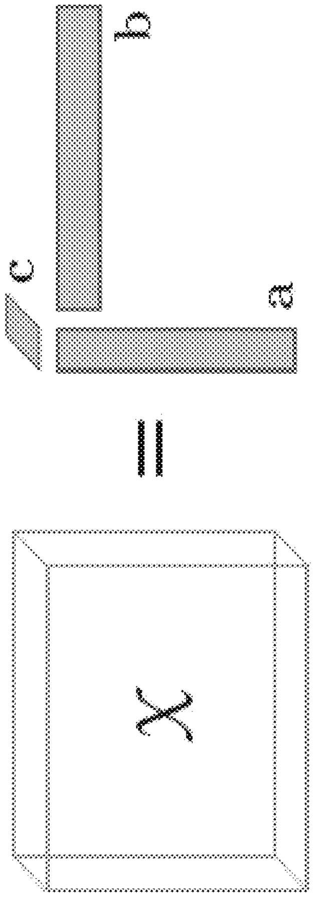
FIG. 3B illustrates an exemplary rank-1 3-way tensor, in accordance with some embodiments.

At block 214, the system runs a CANDECOMP/PARAFAC (CP) tensor factorization for the resulting normalized tensor with target rank $r_1$. The CP tensor factorization (also known as CP tensor decomposition) is a dimensionality reduction method for multiway arrays, which expresses an input tensor as a sum of rank-1 tensors. A N-way tensor is of rank-1 if it can be exactly decomposed into the outer product of N non-zero vectors. A rank-1 3-way tensor can therefore be written as the outer product of 3 non-zero vectors. An exemplary rank-1 3-way tensor is shown in FIG. 3B. One exemplary formulation of the optimization problem solving for the CP tensor factorization is to minimize the Frobenius norm of the error between the matricization of the input tensor and the matricization of its reconstruction through the factor matrices. Then, the optimization problem is solved through block coordinate descent where all but one factor matrices are fixed, and the least-squares solution for the remaining factor matrix is computed, a process which is iteratively followed for all factor matrices in sequence, until convergence. Additional exemplary details of CP tensor factorization can be found in, for example, Carroll, J. Douglas, and Jih-Jie Chang, "Analysis of individual differences in multidimensional scaling via an N-way generalization of "Eckart-Young" decomposition," Psychometrika 35.3 (1970): 283-319; Harshman, Richard A., "Foundations of the PARAFAC procedure: Models and conditions for an" explanatory "multimodal factor analysis," (1970): 1-84; and Hitchcock, Frank L., "The expression of a tensor or a polyadic as a sum of products," Journal of Mathematics and Physics 6.1-4 (1927): 164-189.

Figure 3C:
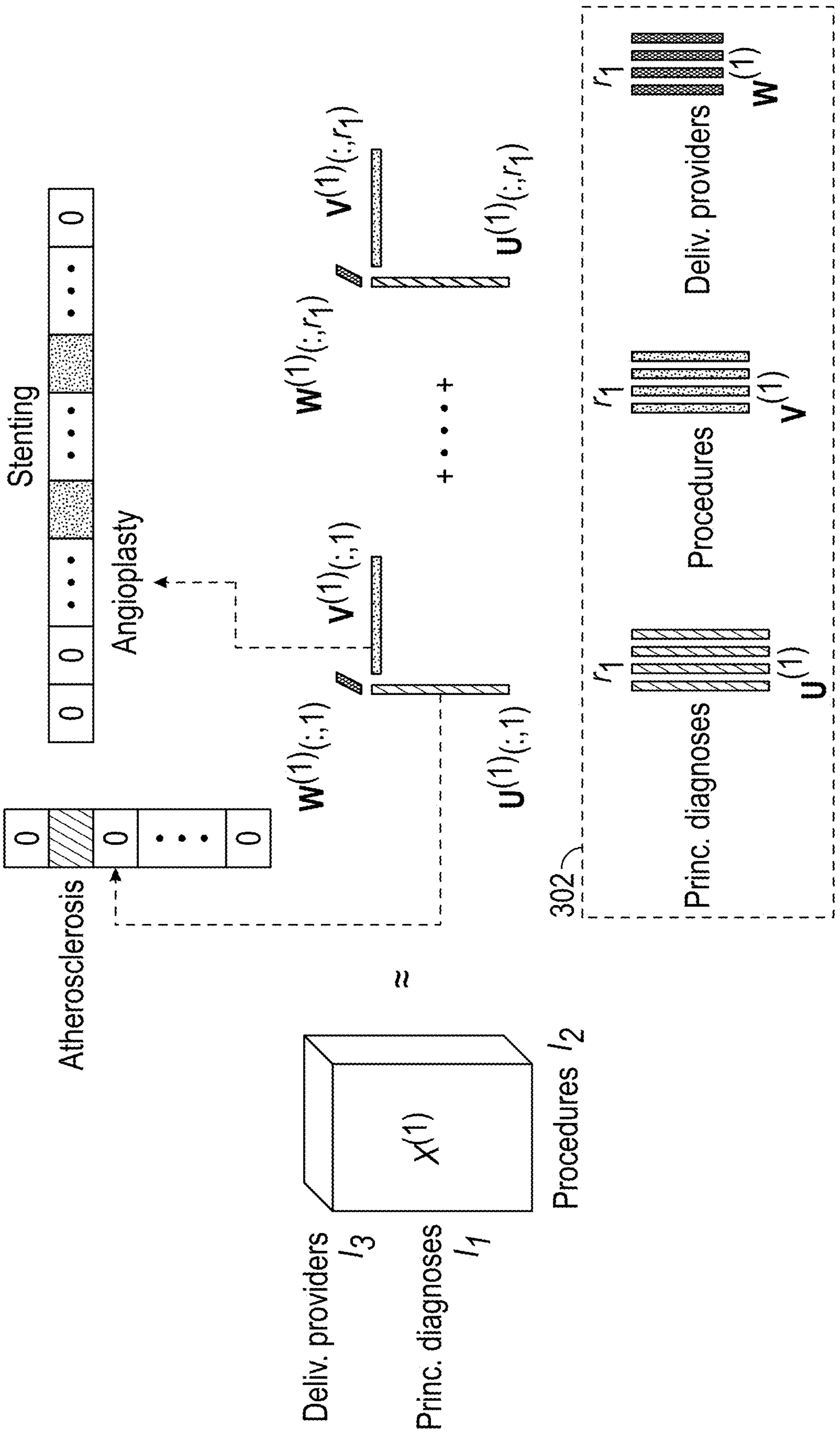
FIG. 3C illustrates an exemplary tensor factorization process to obtain a plurality of rank-1 tensors, in accordance with some embodiments.

FIG. 3C illustrates an exemplary tensor factorization process to obtain a plurality of rank-1 tensors 216. As shown, the tensor (e.g., tensor 210) is factorized or decomposed into $r_1$ number of rank-1 tensors and each rank-1 tensor is expressed as an outer product of three vectors (in red, green, and blue). The red vector contains fields corresponding to principal diagnoses and its length equals the number of unique principal diagnoses (i.e., $l_1$ in the input tensor). The green vector contains fields corresponding to procedures and its length equals the number of unique procedures (i.e., $l_2$ in the input tensor). The blue vector contains fields corresponding to delivering providers and its length equals the number of unique delivering providers (i.e., $l_3$ in the input tensor). The sum of the $r_1$ rank-1 tensors can be used as an approximation of the input tensor.

With reference to 302 of FIG. 3, the red, blue, and green vectors from the rank-1 tensors are grouped into three groups. This leads to the notion of factor matrices $U^{(1)} \in \Re^{l_1 \times r_1}$, $V^{(1)} \in \Re^{l_2 \times r_1}$, $W^{(1)} \in \Re^{l_3 \times r_1}$, where $l_1$, $l_2$, $l_3$ correspond to the number of unique principal diagnoses, procedures and delivering providers respectively (i.e., the dimensions of the input tensor). The $l_1 \times l_2 \times l_3$ elements of the input tensor (i.e., all elements in the cube) are concisely summarized into $(l_1 \times r_1)+(l_2 \times r_1)+(l_3 \times r_1)$ elements of the CP model (i.e., elements in the red, green and blue vectors).

FIG. 3C illustrates the interpretability benefit of using the CP model when non-negative constraints are imposed during training (i.e., the solution of $U^{(1)}$, $V^{(1)}$, $W^{(1)}$ matrices would be constrained to be non-negative). In that case, each of the rank-1 components (i.e., a single set of output vectors the outer product of which forms a single rank-1 tensor, for example $U^{(1)}$ (:, 1), $V^{(1)}$ (:, 1), $W^{(1)}$ (:, 1)) can be interpreted as a single common "normal" utilization pattern of delivering (i.e., attending/rendering) services among the delivering providers within the specialty considered. In particular, given non-negative constraints on the output factors and the example provided in FIG. 3C, an inspection of the vector indices of $U^{(1)}$ (:, 1), $V^{(1)}$ (:, 1) vectors corresponding to non-zero elements leads to interpreting angioplasty and stenting as commonly-used procedures to treat atherosclerosis. Enabling such an interpretation in this context is useful towards model validation/debugging, since one can use domain knowledge to verify whether the "normal" patterns captured do indeed align with some known clinical practice patterns of the corresponding specialty, or whether spurious, noisy patterns have also been contaminating the model captured.

The techniques described herein improve the functioning of computer systems by, for example, reducing usage of computer memory, improving processing power, and improving interpretability while processing a high volume of input (e.g., the input tensor). In particular, given for example an input tensor of size $l_1 \times l_2 \times l_3$, typical matrix factorization-based algorithms would first reshape the tensor into a matrix (e.g., $l_1 \times l_2 l_3$), and then decompose the intermediate matrix into $(l_1+l_2 l_3)r_1$ parameters. In contrast, the CP tensor factorization would directly decompose the input tensor into $l_1 r_1+l_2 r_1+l_3 r_1$ parameters, effectively reducing the memory cost from quadratic to linear with respect to the tensor mode size (assuming that $l_1=l_2=l_3=l$ and $l \gg r_1$). Thus, the techniques described herein improves the functioning of a computer system by allowing computer memory to be efficiently allocated and managed.

Additionally, the CP tensor factorization exhibits superior uniqueness properties, as compared to alternative approaches, such as unconstrained matrix factorization, which typically leads to non-unique models. The issue with non-unique models lies in the fact that there may be several numerically different parameter sets (i.e., sets of factor matrices) which provide equivalent solutions, having the same model fit. Thus, in non-unique models (e.g., matrix factorization without orthogonality constraints), the user would not be able to distinguish which one of the equivalent solutions in terms of approximation error does correspond to the set of ground truth latent factors, which is crucial if the user pursues not only to approximate the input tensor but also to interpret what the latent factors signify, as was described above for the case of the CP model.

Further, the process of interpreting the CP model as described above enables the user to focus only on the $(l_1 \times r_1)+(l_2 \times r_1)+(l_3 \times r_1)$ model coefficients learnt, as opposed to manually processing the full input tensor, a task which may have an asymptotic complexity ranging from the number of non-zero input entries up to $l_1 \times l_2 \times l_3$ in the general case of a dense input. Besides offering a substantially more efficient processing of the input data, the CP model provides a summarization of the input into coefficients, which are highly non-trivial relative to be manually approximated by a user. Such a manually-derived approximation would most likely involve user biases (e.g., reflecting an a priori knowledge of how often does the user expect a certain set of diagnoses and procedures to co-occur), as opposed to a data-driven summarization, enabling detection of anomalous providers based on how their utilization, referral or other patterns compare to those of other providers. Also, any manually-derived approximation of the input tensor lacking a concrete objective criterion to be minimized would most likely result in poor fit (i.e., high approximation error), and thus would be insufficient as a method to capture the most common or "normal" underlying patterns of the input tensor. In sum, the CP tensor factorization offer a mathematically-grounded, easily interpretable and space-efficient approach to summarize an input tensor.

A key observation to note here is that each of the rank-1 components (e.g., the group of vectors $U^{(1)}(:, 1)$, $V^{(1)}(:, 1)$, $W^{(1)}(:, 1)$) corresponds to a single pattern extracted. Thus, there are overall $r_1$ patterns capturing the variation in the input tensor.

Because the factors learned during training (U, V, W) may be constrained to be non-negative, the optimization problem being solved would take those constraints into account and seek for the best (i.e., minimum approximation error) non-negative solutions for the elements of those factors. Imposing non-negative constraints is impactful in practice when the input tensor is non-negative as well (as happens in this case). Considering the reconstruction step through the model factors, it is easy to see that there would be "cancellations" during the reconstruction process (i.e., the reconstruction process is not strictly additive in nature, but also involves subtractions), if the factors contain negative values along with non-negative ones. This severely hinders interpretability, since one cannot know whether the positive values observed in a certain component might actually be cancelled from the negative values observed in another component, and thus the whole notion of trying to interpret combinations of components is too complex, impractical and subject to human errors.

In contrast to the above, having imposed the non-negative constraints (and assuming a non-negative input tensor), the result can be easily interpreted as a sum-of-parts, where the numerical representations of potentially overlapping concepts are added together to approximate the input tensor. As such, it is now reliable to interpret the coordinates corresponding to the largest values of a component vector (e.g., red vector of 1st component) as the elements participating in that component (e.g., atherosclerosis might have a value of 0.8 with the rest of the elements having a value of 0).

At block 216, a reconstruction of the input tensor 210 through the model factors $U^{(1)}$, $V^{(1)}$, $W^{(1)}$ (e.g., the red, blue, and green vectors in FIG. 3) is computed to obtain $Y^{(1)}$. This reconstruction is achieved by calculating the r_1 vector outer products, getting r_1 tensors as partial results and then adding those partial result tensors in an element-wise fashion. Further, the system can calculate a tensor $\varepsilon^{(1)}$ indicating element-wise errors where $\varepsilon^{(1)}(i, j, k)=X^{(1)}(i, j, k)-Y^{(1)}(i, j, k)$. In some embodiments, the system provides a ranked list of the most anomalous features for each provider based on the element-wise errors in tensor $\varepsilon^{(1)}$. For example, in order to detect unexpected over-utilization of (principal diagnosis, procedure) combinations, we would sort the deviations of the matrix $\varepsilon^{(1)}(:,:, k)$ corresponding to the k-th delivering provider and extract the (principal diagnosis, procedure) combinations with the largest positive deviations (multiple heuristics can be defined depending on the embodiment to define the number of anomalous features to return, e.g., computing the cumulative sum of the deviations in descending order and returning the largest deviations accounting for 99% of the sum of all positive deviations). The reasoning behind the aforementioned method of detecting over-utilization of a certain (principal diagnosis, procedure) combination is the following: when a certain $E^{(1)}(i, j, k)$ is positive, it indicates that the input entry $X^{(1)}(i, j, k)$ had an unexpectedly high value which the reconstructed $Y^{(1)}(i, j, k)$ value could not explain based on the model factors. Similarly, the smallest negative values of the matrix $\varepsilon^{(1)}(:,:, k)$ would indicate the (principal diagnosis, procedure) combinations with lower than expected values for the k-th provider, which may also be of interest depending on the embodiment.

At block 218, for the k-th delivering provider, the system computes provider-level deviation for each provider by aggregating the element-wise deviations for the respective provider. In some embodiments, the system can examine the frontal slice of $\varepsilon^{(1)}$ that corresponds to the k-th delivering provider and aggregate the absolute values (or squared values) of element-wise deviations in the frontal slice to obtain a single value. In some embodiments, the system may ignore negative deviation values and compute the provider's deviation score based on positive deviation values only with the goal of detecting over-utilization of services. Thus, for the k-th delivering provider, the system computes a single value indicating the delivering provider's deviation. For all of the delivering providers, the system obtains an array $e^{(1)}$ containing the deviation values of all of the delivering providers.

At block 220, the system normalizes the elements of the array $e^{(1)}$ such that the elements range from 0 to 1. These scores correspond to the output extracted from the pipeline detecting anomalous delivering providers (e.g., 104*a*). The scores are shown as S1 in FIG. 1A.

Figure 2C:
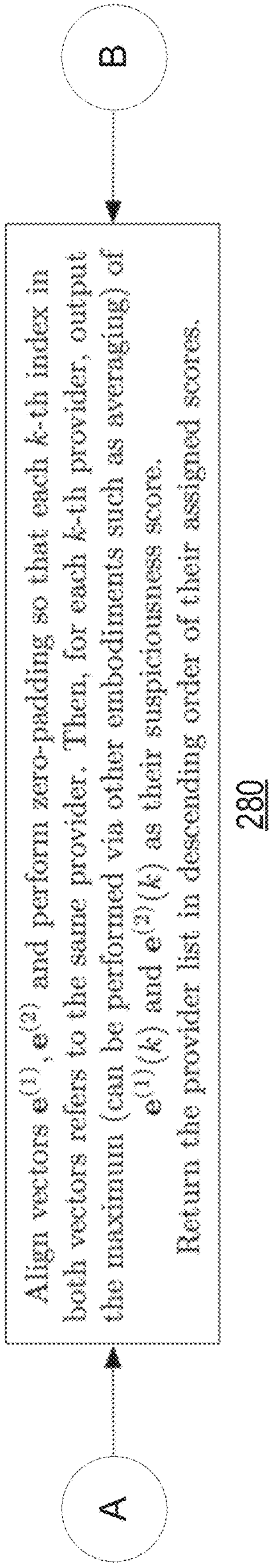
FIG. 2C illustrates an exemplary process for providing a fraud and abuse detection pipeline, in accordance with some embodiments.
Figure 2D:
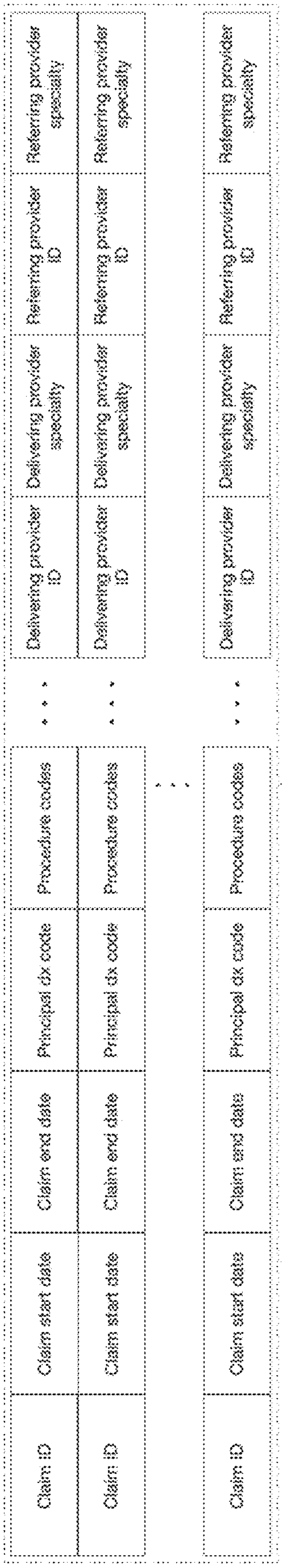
FIG. 2D illustrates an exemplary set of providers data, in accordance with some embodiments.

FIG. 2C illustrates an exemplary process 250 for providing another fraud and abuse detection pipeline, in accordance with some embodiments. The fraud and abuse detection pipeline 250 can be, for example, pipeline 104*b* of FIG. 1A for detecting anomalous providers referring services. The two pipelines 200 and 250 (detecting anomalous delivering and referring providers) can occur in parallel. The pipelines execute the similar methodological steps, with 200 focusing on the delivering providers 250 focusing on the referring providers.

The pipeline parameters 254 can include $r_2$. The target rank is a non-negative integer defining the size of the computed factorization model. Intuitively, $r_2$ indicates how many subgroups of procedures and principal diagnoses are utilized to explain the variation of the providers' referring patterns.

At block 256, the system extracts a subset of providers data 252 based on the pipeline parameters 254. For example, the system can extract claims that 1) occurred during the observation window considered and 2) where the referring provider's specialty is the same as the specialty s given as a pipeline parameter.

At block 258, a second tensor 260 $X^{(2)}$ (i, j, k), of principal diagnoses X procedures X referring providers. Tensor 260 is a multidimensional array, where each (i,j,k) cell is the number of times the k-th referring provider referred for a claim where the j-th procedure code was billed using the i-th principal diagnosis. As shown in FIG. 2B, the tensor 260 is a tensor of order 3 (i.e., a 3-way tensor). The 3-way tensor has lateral, horizontal, and frontal subarrays or "slices," as shown in FIG. 3A.

Blocks 262-270 are performed in similar ways as described above with respect to blocks 212-220. At block 270, the system normalizes the elements of the array $e^{(2)}$ such that the elements range from 0 to 1. These scores correspond to the output extracted from the pipeline detecting anomalous referring providers (e.g., 104*b*). The scores are shown as S2 in FIG. 1A.

With reference to FIG. 2C, at block 280, the scores $e^{(1)}$ and $e^{(2)}$ from the two pipelines are examined together. For each provider, the respective score from $e^{(1)}$ and the respective score from $e^{(2)}$ can be identified and aggregated to obtain an overall score. As described above with reference to FIG. 1A, for each provider, a plurality of scores (e.g., $S_1$-$S_m$ in FIG. 1A) are obtained from the plurality of pipelines. In some embodiments, a single overall score can be obtained for a provider. In some embodiments, the maximum of the provider's scores is retrieved and returned as his or her overall suspiciousness score. In other embodiments, the provider's scores can be combined to calculate the overall suspiciousness score (e.g., taking the average, thresholding the scores, defining rules based on the scores, or by using these scores as inputs to one or more models, etc.).

Accordingly, an overall score for each provider is obtained. In some embodiments, the system returns a list of providers in descending order of their overall scores. In some embodiments, the system can provide one or more user interfaces for: displaying suspiciousness scores of healthcare providers; and organizing suspiciousness scores (e.g., sorting, filtering). In some embodiments, the system can automatically identify a set of providers whose suspiciousness scores are above a certain threshold. This way, the system can triage and prioritize highly suspicious provider instances for manual expert review. In some embodiments, the system can also provide pipeline-specific interpretations of which are the most anomalous features contributing to the pipeline-specific provider's suspiciousness score. In some embodiments, the anomalous features for every suspicious provider can be utilized to flag and potentially deny health insurance claims in real-time. In some embodiments, the system can automatically flag for potential exclusion the set of providers from a database (e.g., in-network benefits) based on the suspiciousness scores. In some embodiments, the system can provide visualizations of healthcare providers based on calculated suspiciousness scores. For example, the system can allow a user to view top suspicious healthcare providers by geographic regions, specialties, etc. As another example, the system can allow a user to view how a provider's suspiciousness scores have evolved over time.

While the processes in FIGS. 2A-C model and identify deviations in characteristic patterns of procedures, diagnoses, settings, referrals, location and scheduling etc. (as well as combinations thereof) the techniques can be readily extended to modeling and identifying deviations in others characteristic patterns of care provision, i.e., across the spectrum of diagnoses, procedures, settings, referrals, scheduling, location and other examples of care provision attributes (as well as combinations and subsets thereof). Further, while the CP tensor model is described above, other tensor factorization models may be used (e.g., Tucker). The CP tensor model can be advantageous due to its interpretability. CP can be easily expressed as a sum of rank-one outer products, where each of the outer products reflects a certain common pattern of the data; in some of the embodiments described in detail, a subgroup of principal diagnoses and procedures along with the associated providers utilizing this subgroup.

Other Approaches Based on Dimensionality Reduction

In addition to or instead of tensor factorization, matrix factorization can be used to arrive at suspiciousness scores for every provider. Instead of modeling each provider through a feature matrix (e.g., a normalized slice in the tensor 210) as in the tensor factorization-based embodiments above, the system can model each provider through a feature vector (e.g., a normalized feature vector) of occurrences of procedures and/or (principal) diagnoses in a feature matrix. An exemplary feature matrix is shown in FIG. 4A.

Based on the above, a pipeline for detecting anomalous providers attending/rendering services can operate as follows: i) factorization of a feature matrix (procedures potentially concatenated with diagnoses), where each (i, j) entry would reflect the (e.g., normalized) number of times the j-th feature appeared in claims where the i-th provider is delivering services, ii) reconstructing the matrix based the learned matrix factors, iii) computation of an error matrix, and iv) summarization of the reconstruction error at a single score for every provider. In the error matrix, each column corresponds to a provider, and the provider's suspiciousness score can be calculated based on the values in the column. Similar to the tensor factorization case described above, in some embodiments, the system provides attribution of the anomaly score to specific features by considering the coordinates of each reconstructed provider vector with the largest error. In some embodiments, the feature matrix corresponds to one of multiple pipelines (corresponding to multiple care provision types). In other embodiments, there is only one pipeline and a single feature matrix is computed across all claims where the provider is delivering, referring, or supporting other care provision types.

Using a vector of a matrix (rather than a matrix of a tensor) to model a provider ignores the co-occurrence between (principal) diagnoses and procedures; thus, the components learned would no longer be constrained to reflect subgroups of procedures occurring in similarly-diagnosed patients. Rather, each component learned might only capture a subset of procedures or diagnoses (and not necessarily the co-occurrence of both). Still, capturing the overall utilization of procedures and/or diagnoses can be useful for the purposes of the present disclosure; for example, it might be considered suspicious if an interventional cardiologist reports PSA tests for the vast majority of their submitted claims (regardless of the associated diagnoses), while those tests are rarely reported by other interventional cardiologists.

Several embodiments can be implemented based on the exact choice of model and objective function for matrix factorization-based anomaly detection. In some embodiments, the factorization step can be implemented based on the singular value decomposition (SVD)/principal component analysis (PCA). In other embodiments, the same step can be implemented via the non-negative matrix factorization (NMF), which would be more preferable towards promoting interpretability (similar to the way non-negative constraints discussed above promote interpretability in tensor factorization). In other embodiments, the same step can be implemented via "robust" variants of the aforementioned models (e.g., mixed-error matrix factorization, robust PCA), where the notion of identifying anomalous entries of the input matrix is encapsulated within the core factorization step. In these embodiments, the objective is to decompose the input matrix into the sum of two sets of factors. The first set corresponds to the learned "normal" patterns and similar assumptions to what has been described about the preferred embodiment hold (i.e., patterns can be concisely summarized into a small number of subgroups of procedures and/or diagnoses). The second set of factors is constrained to be sparse (i.e., small number of non-zeros as compared to the total number of elements); such a constraint naturally enables the corresponding factor(s) to capture anomalous matrix entries, as those entries would deviate from the "normal" patterns and their total number is expected to be small (i.e., sparsity). More broadly, in other embodiments, an autoencoder can be used as the first set of factors (i.e., "normal" patterns), which could capture a concise, non-linear representation of the input providers-by-features matrix, leading to the use of the robust deep autoencoder (RDA) as the anomaly detection module. In that case, the "normal" patterns would be summarized by a feed-forward multi-layer neural network, the parameters of which are trained so that the output approximates the input. Similar to linear models, such as matrix factorization, an autoencoder involves learning a low-dimensional representation of the data ("encoder"), and then projecting a low-dimensional hidden layer back to the higher input dimensions ("decoder", similar to the reconstruction of the input through the factor matrices of matrix factorization). The key idea is that both "encode" and "decode" stages involve non-linear activation functions, thus an autoencoder captures potentially more powerful non-linear, low-dimensional data representations, with the trade-off of being less interpretable, in the sense that it would be more challenging to signify and interpret the most normal or common patterns learnt.

In other embodiments, the aforementioned methods performing dimensionality reduction on a provider-by-features matrix (or tensor, in the general case) can be extended to identify anomalies on a claim level. This would involve generating a claim-by-features matrix populated with claim-level features, such as the presence/absence of diagnostic codes, procedure codes, medication codes, or other data modalities captured within a single claim, which could be further augmented with information about the patient history leading to the submission of the claim (e.g., whether the patient had a certain diagnosis code recorded during the past year). The remaining steps of the pipeline described above can simply be extended to factorizing the claim-by-features matrix, computing the reconstruction error per claim and identifying the most anomalous claims based on the magnitude of the deviation of a claim's input feature vector from its reconstruction through the factorization model's factors. The claims found to be anomalous based on the reconstruction error measure can be aggregated on a provider level to identify the most anomalous providers (e.g., based on the percentage of a provider's claims which have been flagged with relatively large reconstruction errors). Additionally, the learnt model's factors (e.g., singular vectors in the case of the singular value decomposition) can be used to project incoming claim feature vectors and identify anomalous claims in a production setting, as the ones exceeding a certain reconstruction error threshold.

In some embodiments, a single model can be trained across all claims sharing the same value across a particular feature (e.g., presence of a particular procedure code). The choice of that feature for each of the models might vary across embodiments and may be informed by domain knowledge (e.g., targeting specific procedure codes which may be typically abused). Such an approach may provide a simpler and more interpretable extraction of flagged patterns per claim/provider, as the flagged pattern would essentially correspond to the feature, the value of which is shared across the input claims. For example, a provider would be flagged for suspicious utilization of COVID-19 testing, if they have been flagged as anomalous across the claims sharing COVID-19 testing occurrence (e.g., due to potential addition of unnecessary procedures across most of their COVID-19 tests reported, which rarely co-occur with COVID-19 testing across claims from other providers).

The term "factorization" herein refers to any dimensionality reduction techniques, including tensor factorization, matrix factorization, auto encoder-based approaches.

Other Approaches for Anomaly Detection

Once the providers-by-features matrix is computed for delivering, referring, and/or other pipelines, alternative unsupervised techniques can be utilized to implement the anomaly detection. Such techniques include, but are not limited to: one-class support vector machine (SVM) and support vector data description (SVDD), isolation forest (iForest), nearest-neighbor based techniques such as the local outlier factor (LOF), clustering-based anomaly detection, as well as histogram-based techniques such as the histogram-based outlier score (HBOS).

Apart from unsupervised machine learning approaches detecting anomalous providers based on receiving the provider-by-features matrix capturing delivering, referring, or other provider care patterns as input, distribution-based anomaly detection techniques may be used in some embodiments. In this category of methods, assumptions are imposed with respect to the type of the underlying feature distribution for each provider, and providers who deviate from those distributional assumptions are considered as anomalous. For example, the Mahalanobis method can be used where the assumption is that each data point (provider) follows a multivariate normal distribution and the Mahalanobis distance of each data point to the data centroid is computed as the anomaly score. The output of this approach can comprise the data points (providers) exceeding a certain threshold in terms of the Mahalanobis distance, who would be considered as anomalous.

Univariate statistical approaches can also be used, in other embodiments, to detect anomalous providers based on a provider's behavior across each feature individually. As an illustrative example, consider the use case of detecting providers with an anomalous utilization of procedures, as compared to other providers within the same specialty. In this case, the rows of the input matrix would correspond to the various providers sharing the same specialty and the columns would correspond to features indicating the utilization of various procedures (e.g., rates of utilization, frequency of utilization, etc.). In this category of univariate approaches (i.e., detecting anomalies per each feature in isolation from the rest of the input features), the output can comprise a list of providers considered to be anomalous based on at least a single feature; in addition to that list, for each provider, a list of the features based on which they were deemed to be anomalous would also be provided as an output. In some embodiments, where a certain feature can be assumed to be normally distributed across providers within the same specialty, the z-score of each provider across that feature can be computed (subtracting each provider's feature value by the mean value of that feature and dividing by the feature's standard deviation) and (provider, feature) combinations with a z-score exceeding a certain threshold may be flagged as anomalous. In some cases, the impact of anomalies may contaminate the estimates of mean and standard deviation (towards computing the z-scores), so that a typical z-score may not reflect a representative provider anomaly score (e.g., a single or a few extreme values may significantly distort the estimate of the distribution mean); in those cases, robust central tendency and scale estimators, such as the median and the median absolute deviation, can be used instead to compute robust z-score variants. Other outlier-resistant approaches which depend on the percentiles/quartiles can also be used, such as to define anomalies based on the boxplot approach. In cases when the underlying feature distribution may be skewed (e.g., lognormal distribution), then the adjusted boxplot approach can be utilized instead, which explicitly takes distribution skewness into account by accordingly modifying the thresholds based on which a data point is called out as an anomaly (i.e., boxplot fence values). In some embodiments, the medcouple can be used as a robust measure of distribution skewness. Additional conditions may be employed across embodiments using approaches based on the (adjusted) boxplot, in cases when the interquartile range of the underlying feature distribution is equal to zero. In those cases, any provider with a feature value greater (lower) than the third (first) quartile would be flagged as anomalous, which may introduce a large number of falsely-flagged providers. In some embodiments, when the interquartile range is equal to zero, an additional condition may be employed so that only providers with feature values greater (lower) than a certain percentile (e.g., 95th) would be flagged.

Supervised learning approaches can also be utilized as subroutines to tackle this anomaly detection problem through the attribute-wise learning for scoring outliers (ALSO) method. In some embodiments, a plurality of regression models corresponding to a plurality of features can be generated. Each regression model is trained to predict a respective individual feature by using all the remaining features. For example, if the plurality of features are [feature 1, feature 2, . . . feature n], a model can be trained to receive [feature 2, . . . , feature n] of a provider to predict feature 1 of the provider. The plurality of features can include any feature related to medical practice of a provider, such as the number of their members having received a certain procedure, the number of their members having received a certain medication prescription, or other features related to the provider's billing/care patterns.

The training dataset can comprise historical claims reflecting care/billing patterns aggregated on a provider level from a plurality of providers. The training of the models can be performed by linear regression, polynomial regression, factorization machines, support vector regression, k-nearest neighbors regression, tree-based or neural network-based regression approaches, to name a few examples.

After the models are trained, data related to a specific provider can be provided to each of the models. The data can include, for example, the number of the specific provider's members with certain diagnoses, the number of the specific provider's members having received a certain procedure, the number of the specific provider's members having received a certain medication prescription, or other features related to the specific provider's billing/care patterns.

Each model of the plurality of models can output a predicted feature. For each model, a feature deviation can be calculated based on the difference between the predicted feature and the provider's actual value. An average of all feature deviations can be used as the provider's suspiciousness score. In some embodiments, the average can be normalized and/or weighted.

Certain embodiments of the invention may be realized by focusing on only a subset of features as regression targets (e.g., most meaningful features regarding the specialty considered). For example, a regression model can be configured to only receive the count of a provider's members with a certain diagnosis code as inputs and output the predicted count of members with a certain procedure furnished or referred from the provider (e.g., to identify cases where the number of a provider's referrals for a certain procedure cannot be explained by the types of patients they have an office visit with). The training dataset can comprise historical claims data containing the corresponding features (number of members with a certain diagnosis coded, number of members with a certain procedure furnished or referred, etc.) aggregated on a provider level from a plurality of providers. After the model is trained, a specific provider's counts of a provider's members with a certain diagnosis code is inputted to the model to obtain a predicted count of members with a certain procedure furnished or referred from the provider. The predicted count is compared with the specific provider's actual count. The feature deviation can be indicative of the provider's score.

In other embodiments, the percentage or the count of a provider's members with certain diagnoses (or derived diagnostic features, such as comorbidities), or medications prescribed can be used as the model features and each procedure or medication utilization (or additional information such as cost per procedure, per medication or total provider cost) can be used as the regression target, with the intent of identifying provider cases where the diagnoses (or comorbidities, or other measure of patient complexity) of their patients would not explain a certain procedure's or medication's high utilization or overall provider cost. For example, a regression model can be configured to receive the number of a provider's members where certain low-cost medications are received as inputs and output the utilization (e.g., the number of members where the drug is prescribed) of expensive, specialty drugs or the total cost of prescriptions for the provider's members, as a way to identify whether certain lower cost alternatives have been used as part of a step therapy before prescribing expensive, specialty medications. The training dataset can comprise of medical and/or pharmacy historical claims aggregated on provider level. The predicted output(s) can be compared against the provider's actual activities to derive a score for the provider.

In the context of supervised learning approaches, classification methods can also be utilized to identify anomalies either on a provider or on a claim level. For example, a classification model can be configured to receive a plurality of features of a particular provider, such as indicators reflecting the provider's specialty (or other prior knowledge about the provider) or derived features based on the provider's billing/care patterns), and output a probability or indicator of whether a certain procedure code (or other indicator of care pattern) is expected to be billed based on the features of that particular provider. As another example, a classification model can be configured to receive a plurality of features of a particular claim and output a probability or binary indicator of whether a certain procedure code (or other indicator of care pattern) is expected as part of that particular claim.

Classification methods which could be used include, but are not limited to: Logistic Regression, Naïve Bayes, k-Nearest Neighbors, Decision Trees (and tree-based approaches in general), Support Vector Machines, neural network-based approaches.

In some embodiments, the training set can comprise a set of claims and the target can be to predict the presence or absence of a certain feature (e.g., procedure code, diagnostic code, medication code). The claim feature vectors would be derived based on historical claims data, and may be additionally augmented by information about the past history of the patient leading to the submission of each claim (e.g., how many times was the procedure under prediction administered to the patient in the past year, when was the last time this procedure was administered to the patient, when was the last time the patient visited the same provider to the one listed in the current claim). The choice of prediction targets across the individual models trained may be guided by domain knowledge (e.g., procedures being typically abused by providers). For example, certain types of genetic or drug tests may be of particular interest, as being frequently abused.

Then, the cases in which the model prediction indicates a highly-confident disagreement with the ground truth could be used to surface anomalous claims (and accordingly anomalous providers by grouping flagged claims on a provider level). For example, if the classification model predicts a low probability that the provider will bill to a certain procedure code (e.g., the probability is below a predefined threshold) but the provider did bill to the procedure code, the system can flag the provider as suspicious. For example, if the classification model predicts a low probability that the provider will order a drug test (e.g., the probability is below a predefined threshold) but the provider did order the drug test, the system can flag the provider as suspicious.

Prediction confidence may be reliably captured either via models which natively assign well-calibrated, probabilistic scores to each of the test set instances (e.g., Logistic Regression), or through post-hoc calibration approaches (e.g., binning, Platt scaling). For example, through the histogram binning approach, the raw prediction scores of a classification method are first sorted and then partitioned into bins of equal size, so that each one of the bins contains approximately the same number of data points. For each one of the bins, a certain lower and upper bound of raw prediction score is computed. For each one of the test data points, the bin it should be assigned to is found by comparing the raw prediction score to the lower and upper bin bounds. Finally, the corrected probability for the test point is returned as the fraction of positively labeled instances contained in the assigned bin. In some embodiments, a calibration set may be used to compute the lower and upper bin bounds which is separate from the training set, used to originally train the model.

In other embodiments, a multi-class classification approach may be utilized to specifically target potential upcoding (e.g., identify cases when an office visit's level of complexity is lower than what the provider submitting the claim indicates, or cases when a certain procedure is billed at the highest level of complexity when in fact the associated claim's diagnosis codes cannot justify that). For example, multinomial logistic regression may be trained to predict the complexity of an office visit (e.g., 5 levels of complexity, depending on how much time the provider spends or other factors of patient complexity), using the diagnoses, procedures and other data submitted as part of a certain claim. For each one of the test points (incoming claims of office visits), the level of complexity to which the highest probabilistic score is assigned would be considered as the predicted level of complexity for the corresponding claim. Claims with high positive difference between the true and the predicted level of complexity (e.g., level-5 vs level-3 would result in a +2 difference) may indicate potential upcoding attempted on behalf of the provider submitting them and be assigned a suspiciousness score accordingly.

Figure 4B:
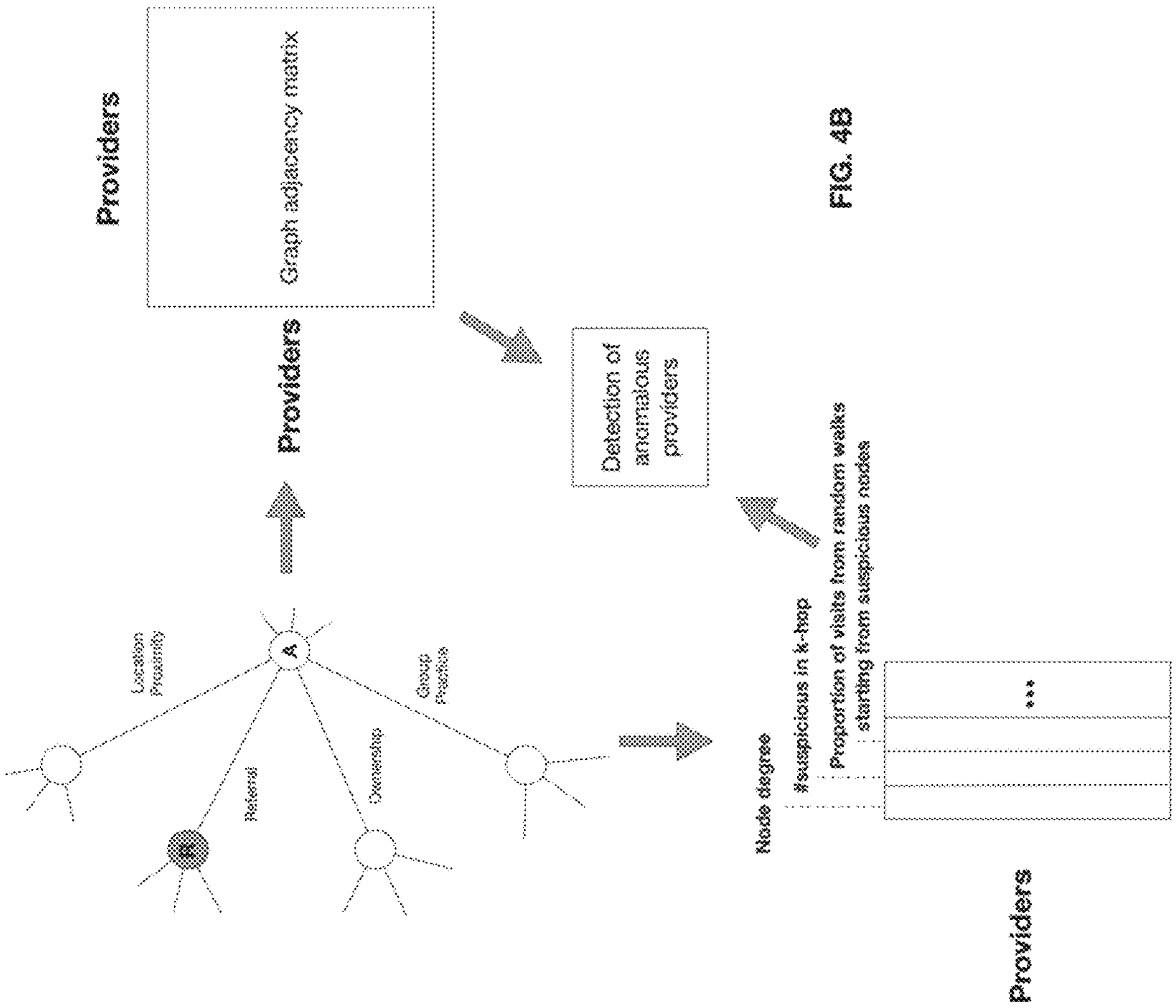
FIG. 4B illustrates an exemplary graph, in accordance with some embodiments.

In some embodiments, alternative data representations can be used and in turn, different methodologies may be utilized to extract features for every provider within a specialty. For example, apart from analyzing the services referred by every provider, in some embodiments, features may be extracted for every referring provider based on the referral graph; each node in this graph would correspond to a provider and an edge (i, j) would represent that the i-th provider has referred one or more patients to the j-th provider. Graph-based features are useful since they capture long-range correlations among connected providers, as those are reflected by the potentially multiple paths connecting them. For each provider, examples of graph features which can be used in some embodiments contain, but are not limited to: counting the number of connected nodes (i.e., node degree), counting the number of nodes in the k-hop neighborhood (k=1, 2, 3, . . . ), calculating the ratio between a node's degree and the number of edges among all nodes in the 1-hop neighborhood of the node, counting the number of nodes in the k-hop neighborhood having a certain characteristic (e.g., guided by rule-based knowledge as we describe below), estimating the node's probability of being visited by random walks starting from a set of nodes having a certain characteristic (e.g., guided by rule-based or external knowledge indicating a node as fraudulent). Apart from information regarding the referrals, in some embodiments, several other types of provider connections can be modeled through a graph, such as: a) measuring the distance between the business practice locations among different providers and if the distance among a pair of providers is lower than a threshold then those providers are connected through an edge; b) providers who share the same group practice are connected to a node representing the group practice; c) the owner of a certain facility is connected to the providers being part of that facility. All the above pieces of information can be modeled via a single graph, capturing all the possible provider connections, in some embodiments. FIG. 4B illustrates an example of such a graph, where various types of relationships among graph nodes are captured, such as proximity in terms of location of business practices, whether a provider has provided referrals to another provider, whether a provider/individual is the owner of a business practice where another provider is practicing, as well as whether two providers share the same group practice. The node annotated as "R", colored in red, corresponds to an example of a suspicious provider (e.g., based on external knowledge, rules, or insights derived through anomaly detection). The bottom left of FIG. 4B illustrates a matrix created to capture graph-based provider features, i.e., each row corresponds to a certain provider and each column corresponds to a different feature. Any anomaly detection method discussed in the context of the present disclosure which admits an input matrix of providers X features can be used to detect anomalous providers, as well as their most anomalous features, depending on the embodiment. Also, as long as an adjacency matrix of a graph can be computed indicating the weight or the existence of an edge (with the value of zero corresponding to the absence of an edge), then factorization-based approaches can be used on top of the adjacency matrix to detect outlying edge values. For example, when using non-negative matrix factorization, the different factors would capture various graph communities, and the reconstruction of the input based on the learnt factors would reveal edges which would be expected to be present in the input graph, as well as edges which are present but cannot be explained based on the graph structure. Based on such a pipeline, in some embodiments, an outlier score per provider based on the adjacency matrix can be computed as a sum over all residual edge values associated to that provider.

Incorporating External Knowledge in the Form of Rules

Getting access to gold-standard labels of fraud and/or abuse, characterized by substantial amount and diversity, is an extremely challenging task, due to the scarcity of such labels. Instead, the extraction of "soft" rule-based labels derived through domain knowledge is a more realistic approach in order to obtain provider suspiciousness scores which would be partially grounded on domain knowledge; those labels would differentiate between what should or should not be considered as a "normal" provider's pattern. Such examples of rules flagging "non-normal" behavior based on domain knowledge include, but are not limited to: a) a referring provider who has no visit records by the patient being referred before the date of the service being referred for (combined with further conditions such as whether the referring provider's business practice is relatively far from the patient's home address, referring provider not being from the same group practice as delivering provider or any other provider who has seen the patient in the past, etc.); b) a delivering provider who is conducting a certain test too frequently for their members as compared to the general frequency guidelines of that particular test (e.g., myocardial perfusion imaging testing occurring too frequently); c) a delivering provider who is conducting procedures which are not justified given the patient history and comorbidities (e.g., cardiac stress tests in patients without any prior cardiac symptoms); d) a delivering provider performing procedures that patients are not eligible for; e) a delivering/referring provider who has been sanctioned; f) a delivering provider who reports an unusually high number of new patients in a short period of time; g) a referring provider who provides an unusually high number of referrals in a short period of time; h) a delivering (referring) provider with an unusually high number of out-of-state patients (referred); i) a delivering (referring) provider with an unusually high number of concurrent state licenses issued (potentially indicating a fraudulent intent regarding filing (referring for) false claims for members across several, different states); j) a delivering (referring) provider with an unusually high number of claims submitted for a certain procedure, which is used across very few other providers within the provider's specialty.

In one embodiment, the system can perform unsupervised anomaly detection by identifying providers with care provision patterns that do not conform to "normal" behavior as per these rules. In another embodiment, we can incorporate rule-based knowledge as part of our anomaly detection framework, and can exclude delivering/referring providers with positive labels (i.e., "non-normal") from the training data during the training process for building models of normal care provision patterns (from which deviations are detected). The intuition behind this semi-supervised approach is that the learned "normal" patterns of billing/referral practices (e.g., factors of tensor factorization) would not be contaminated by potentially noisy or suspicious providers. Then, we can compute how the left-out providers are represented with respect to the learned patterns. Note that the precise implementation of this step varies depending on the particular embodiment; for example, in a tensor/matrix factorization-based approach, a vector is computed for each left-out provider to indicate their utilization of each of the learned patterns. Intuitively, in the tensor/matrix factorization approach involving non-negative constraints (as discussed above in one of the embodiments), the factor matrices indicating the low-rank representation of each type of features used are fixed (e.g., the matrices $U^{(1)}$ and $V^{(1)}$ in FIG. 3C) and a solution for the factor matrix corresponding to the low-rank representation of each input provider is sought ($W^{(1)}$ matrix in FIG. 3C). Each row $W^{(1)}$ (k,:) indicates to what extent the k-th input provider utilizes each of the r_1 learned patterns. As another example, using an isolation forest, the number of edges from the root to a leaf node (i.e., without any child nodes) is computed as the left-out provider instance traverses across a learned tree.

Another way of incorporating external knowledge in the form of rules can be realized by adding additional pipelines that flag providers based on a certain rule (or a combination of them). Without loss of generality, through each of the rule-based additional pipelines, a suspiciousness score can be computed as the fraction of relevant claims satisfying the rule. For example, one such pipeline could compute the number of a delivering provider's claims where the listed procedures cannot be justified based on the patient history (e.g., cardiac stress tests in patients without related symptoms) and the associated provider's score can be computed as the fraction of the provider's total number of submitted claims where this suspicious pattern is observed.

Finally, one more way of incorporating rule-based external knowledge is by designing pipelines feeding rule-based features into an anomaly detection framework. For example, in a certain embodiment, features indicating billing, referral and "non-normal" rule-based patterns can be computed for each provider. Note that such concatenation of multiple different views including features with different missingness levels and/or potentially different correlation structures would not be the preferred embodiment of the invention in the general case. However, depending on the particular anomaly detection method used and features incorporated, such an approach might be suitable. Multi-view anomaly detection approaches could also be used under this setup, which do take into account the different characteristics of each one of the data views considered.

Figure 5:
FIG. 5 illustrates the process for detecting anomalous healthcare providers, according to various embodiments.

FIG. 5 illustrates process 500 for detecting anomalous healthcare providers, according to various examples. Process 500 is performed, for example, using one or more electronic devices implementing a software platform. In some examples, process 500 is performed using a client-server system, and the blocks of process 500 are divided up in any manner between the server and a client device. In other examples, the blocks of process 500 are divided up between the server and multiple client devices. Thus, while portions of process 500 are described herein as being performed by particular devices, it will be appreciated that process 500 is not so limited. In other examples, process 500 is performed using only a client device or only multiple client devices. In process 500, some blocks are, optionally, combined, the order of some blocks is, optionally, changed, and some blocks are, optionally, omitted. In some examples, additional steps may be performed in combination with the process 500. Accordingly, the operations as illustrated (and described in greater detail below) are exemplary by nature and, as such, should not be viewed as limiting.

At block 502, the system (e.g., one or more electronic devices) constructs, based on the first care provision type, a first data structure based on medical claims data of a plurality of healthcare providers. At block 504, the system automatically performs factorization on the first data structure to obtain a set of data structures, wherein the set of data structures is indicative of one or more common patterns among the plurality of healthcare providers. At block 506, the system automatically, based on the set of data structures, obtains a second data structure, wherein the second data structure is indicative of deviation by the plurality of healthcare providers from the one or more common patterns. At block 508, the system calculates, based on the second data structure, a score for a particular provider of the plurality of providers, wherein the score is indicative of an amount of deviation of the particular provider from the one or more common patterns when providing the first care provision type. At block 510, the system causes display of the particular provider based on the score.

Figure 6:
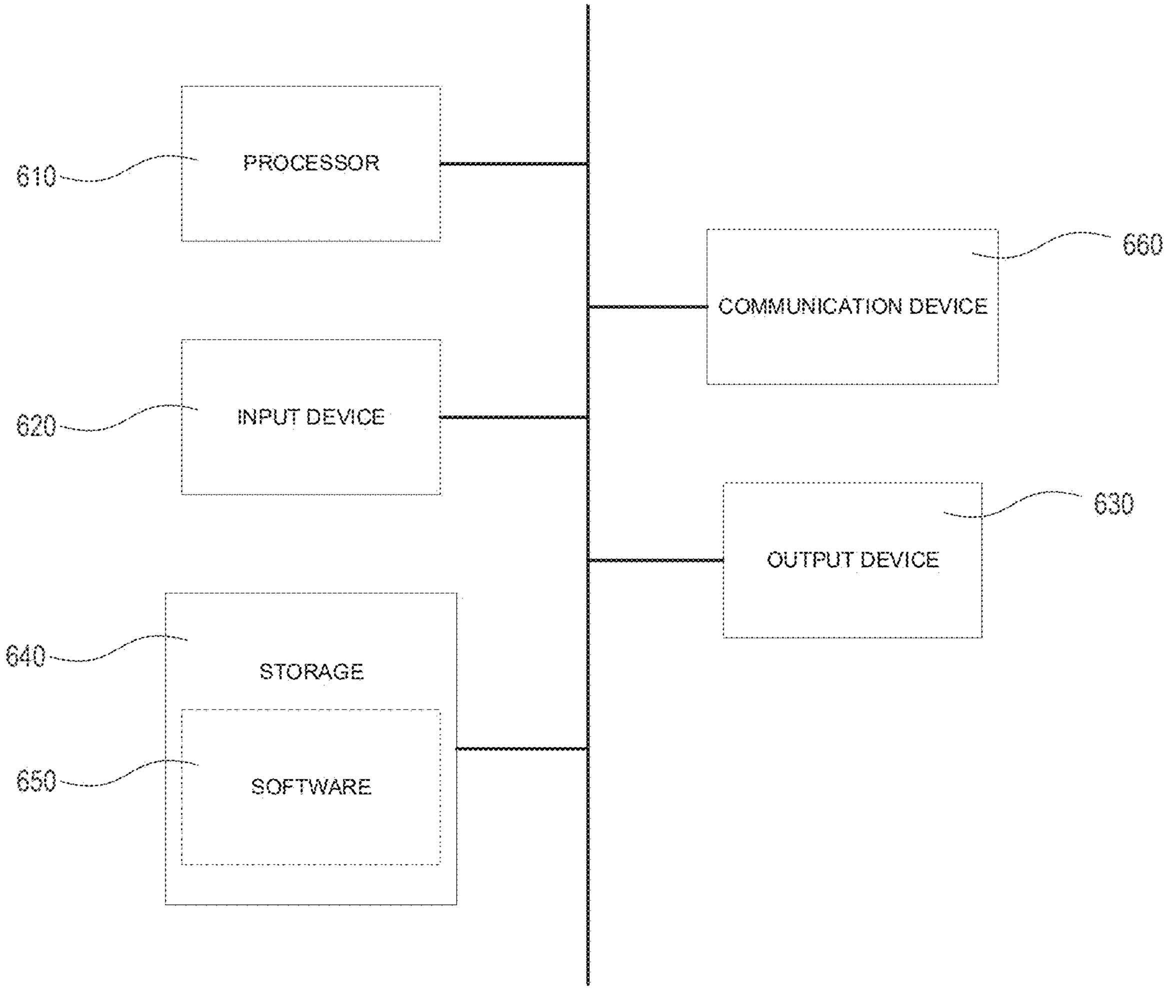
FIG. 6 depicts an exemplary electronic device in accordance with some embodiments.

The operations described above with reference to FIG. 5 are optionally implemented by components depicted in FIG. 6. It would be clear to a person having ordinary skill in the art how other processes are implemented based on the components depicted in FIGS. 1-5.

FIG. 6 illustrates an example of a computing device in accordance with one embodiment. Device 600 can be a host computer connected to a network. Device 600 can be a client computer or a server. As shown in FIG. 6, device 600 can be any suitable type of microprocessor-based device, such as a personal computer, workstation, server or handheld computing device (portable electronic device) such as a phone or tablet. The device can include, for example, one or more of processor 610, input device 620, output device 630, storage 640, and communication device 660. Input device 620 and output device 630 can generally correspond to those described above, and can either be connectable or integrated with the computer.

Input device 620 can be any suitable device that provides input, such as a touch screen, keyboard or keypad, mouse, or voice-recognition device. Output device 630 can be any suitable device that provides output, such as a touch screen, haptics device, or speaker.

Storage 640 can be any suitable device that provides storage, such as an electrical, magnetic or optical memory including a RAM, cache, hard drive, or removable storage disk. Communication device 660 can include any suitable device capable of transmitting and receiving signals over a network, such as a network interface chip or device. The components of the computer can be connected in any suitable manner, such as via a physical bus or wirelessly.

Software 650, which can be stored in storage 640 and executed by processor 610, can include, for example, the programming that embodies the functionality of the present disclosure (e.g., as embodied in the devices as described above).

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 600 can implement any operating system suitable for operating on the network. Software 650 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Exemplary methods, non-transitory computer-readable storage media, systems, and electronic devices are set out in the following items:

1. A computer-implemented method for automatically detecting anomalous healthcare providers, comprising:

in a first pipeline corresponding to a first care provision type:

constructing, based on the first care provision type, a first data structure based on medical items data of a plurality of healthcare providers;

automatically performing factorization on the first data structure to obtain a set of data structures, wherein the set of data structures is indicative of one or more common patterns among the plurality of healthcare providers;

automatically, based on the set of data structures, obtaining a second data structure, wherein the second data structure is indicative of deviation by the plurality of healthcare providers from the one or more common patterns;

calculating, based on the second data structure, a score for a particular provider of the plurality of providers, wherein the score is indicative of an amount of deviation of the particular provider from the one or more common patterns when providing the first care provision type;

causing display of the particular provider based on the score.

2. The method of item 1, wherein the first data structure comprises a tensor.

3. The method of item 2, wherein the tensor comprises a multi-dimensional array, wherein each cell is an exact or normalized count for each provider or a combination of providers of the occurrence of a specific combination of care provision characteristics.

4. The method of item 3, wherein the tensor comprises a three-dimensional array, wherein each (i,j,k) cell is the number of times the k-th provider billed for the j-th procedure code using the i-th principal diagnosis.

5. The method of item 2, wherein the set of data structures comprises a set of rank-1 tensors.

6. The method of item 2, wherein the factorization is a CANDECOMP/PARAFAC (CP) tensor factorization.

7. The method of item 1, further comprising: receiving a user input indicative of a specialty, wherein the plurality of providers is selected based on the specialty.

8. The method of item 2, wherein the second data structure comprises a reconstruction error tensor.

9. The method of item 8, further comprising:

identifying a slice of the reconstruction error tensor, wherein the slice corresponds to the particular provider; and calculating the score for the particular provider based on the slice.

10. The method of item 9, further comprising calculating scores of features (or their co-occurrence with other features) based on the slice.

11. The method of item 9, wherein the score is a maximum value of the slice, an average of the slice, or a combination thereof.

12. The method of item 1, wherein the first data structure is a feature matrix.

13. The method of item 1, wherein the score is a first score, the method further comprising:

in a second pipeline corresponding to a second care provision type:

constructing, based on the second care provision type, a third data structure based on healthcare items data of the plurality of healthcare providers;

calculating, based on the third data structure, a second score for the particular provider of the plurality of providers, wherein the score is indicative of an amount of deviation by the particular provider from the one or more common patterns when providing the second care provision type;

calculating an overall score for the particular provider based on the first score and the second score; and causing display of the particular provider based on the overall score.

14. The method of item 1, further comprising automatically ranking the plurality of providers.

15. The method of item 1, wherein the first care provision type comprises: delivering services, referring services, scheduling services, or sourcing patients to locations.

16. The method of item 1, further comprising:

obtaining, based on the second data structure, one or more anomalous features corresponding to the particular provider;

receiving data corresponding to a healthcare item by the particular provider;

comparing the one or more anomalous features with the healthcare item; and flagging the healthcare item if there is an overlap between the healthcare item and the one or more anomalous features.

17. An electronic device, comprising:

one or more processors;

a memory; and one or more programs, wherein the one or more programs are stored in the memory and configured to be executed by the one or more processors, the one or more programs including instructions for:

in a first pipeline corresponding to a first care provision type:

constructing, based on the first care provision type, a first data structure based on medical items data of a plurality of healthcare providers;

automatically performing factorization on the first data structure to obtain a set of data structures, wherein the set of data structures is indicative of one or more common patterns among the plurality of healthcare providers;

automatically, based on the set of data structures, obtaining a second data structure, wherein the second data structure is indicative of deviation by the plurality of healthcare providers from the one or more common patterns;

calculating, based on the second data structure, a score for a particular provider of the plurality of providers, wherein the score is indicative of an amount of deviation of the particular provider from the one or more common patterns when providing the first care provision type;

causing display of the particular provider based on the score.

18. A non-transitory computer-readable storage medium storing one or more programs, the one or more programs comprising instructions, which when executed by one or more processors of an electronic device having a display, cause the electronic device to:

in a first pipeline corresponding to a first care provision type:

constructing, based on the first care provision type, a first data structure based on medical items data of a plurality of healthcare providers;

automatically performing factorization on the first data structure to obtain a set of data structures, wherein the set of data structures is indicative of one or more common patterns among the plurality of healthcare providers;

automatically, based on the set of data structures, obtaining a second data structure, wherein the second data structure is indicative of deviation by the plurality of healthcare providers from the one or more common patterns;

calculating, based on the second data structure, a score for a particular provider of the plurality of providers, wherein the score is indicative of an amount of deviation of the particular provider from the one or more common patterns when providing the first care provision type;

causing display of the particular provider based on the score.

19. A computer-implemented system for automatically detecting anomalous healthcare providers and anomalous healthcare items, comprising:

in a first pipeline corresponding to a first set of care provision characteristics:

constructing, based on the first set of care provision characteristics, a first data structure based on healthcare items data of a plurality of healthcare providers;

automatically performing factorization on the first data structure to obtain a set of data structures, wherein the set of data structures is indicative of the one or more common patterns among the plurality of healthcare providers;

automatically, based on the set of data structures, obtaining a second data structure, wherein the second data structure is indicative of deviations by the plurality of healthcare providers from the one or more common patterns;

calculating, based on the second data structure, a score for a particular provider of the plurality of providers or a particular healthcare item of a plurality of healthcare items, wherein the score is indicative of an amount of deviation of the particular provider or the particular item from the one or more common patterns when providing the first care provision type;

causing a set of actions to be executed based on the score.

20. The method of item 19, wherein the care provision characteristics include diagnostic information, procedural information, setting information, scheduling information, referral information, location information, ownership information and combinations thereof.

21. The method of item 19, wherein the first data structure comprises a tensor.

22. The method of item 21, wherein the tensor comprises a multi-dimensional array, wherein each cell is an exact or normalized count for each provider or for a combination of providers of the occurrence of a specific combination of care provision characteristics.

23. The method of item 21, wherein the set of data structures comprises a set of rank-1 tensors.

24. The method of item 21, wherein the factorization is a CANDECOMP/PARAFAC (CP) or a Tucker tensor factorization.

25. The method of item 21, wherein the second data structure comprises a reconstruction error tensor.

26. The method of item 25, further comprising:

identifying an array of the reconstruction error tensor, wherein the array corresponds to the particular provider; and calculating the score for the particular provider based on the array; and calculating scores of features or their co-occurrence with other features based on the array.

27. The method of item 26, wherein the score is a maximum value of the array, an average of the array, a sum of the array, a sum of the absolute values of the array, a sum of either of the positive or the absolute values of the negative values of the array, a sum of the output of a function over each value of the array, wherein the function is configured to receive the corresponding error values for all providers and compute deviations from one-dimensional summary statistics or order statistics.

28. The method of item 19, wherein the set of data structures comprise an autoencoder.

29. The method of item 28, wherein the second data structure comprises a reconstruction error matrix.

30. The method of item 28, wherein the autoencoder is a robust deep autoencoder.

31. The method of item 30, further comprising: identifying a vector of the reconstruction error matrix, wherein the vector corresponds to the particular provider; and calculating the score for the particular provider based on the vector, and calculating scores of features based on the vector.

32. The method of item 19, wherein the first data structure comprises a feature matrix.

33. The method of item 32, wherein the factorization is implemented based on singular value decomposition, principal component analysis or non-negative factorization.

34. The method of item 32, wherein the second data structure comprises a reconstruction error matrix.

35. The method of item 34, further comprising: identifying a vector of the reconstruction error matrix, wherein the vector corresponds to the particular provider; and calculating the score for the particular provider based on the vector, and calculating the scores of features based on the vector.

36. The method of item 19, further comprising: receiving a user input indicative of a specialty, wherein the plurality of providers is selected based on the specialty.

37. The method of item 19, further comprising: receiving a user input indicative of a geography, wherein the plurality of providers is selected based on the geography.

38. The method of item 19, further comprising: receiving a user input indicative of a line of business, such as Medicare, Medicaid, Commercial, Family, Individual or Employer health insurance, wherein the plurality of providers is selected based on the line of business.

39. The method of item 19, wherein the score is a first score, the method further comprising:

in a second pipeline corresponding to a second set of care provision characteristics:

constructing, based on the second set of care provision characteristics, a third data structure based on healthcare items data of the plurality of healthcare providers;

calculating, based on the third data structure, a second score for the particular provider of the plurality of providers or the particular healthcare item of a plurality of healthcare items, wherein the score is indicative of an amount of deviation by the particular provider or the particular item from the one or more common patterns when providing the second care provision type;

calculating an overall score for the particular provider or the particular item based on the first score and the second score; and causing a set of actions to be executed based on the overall score.

40. The method of item 19, wherein the set of actions to be executed include pre-pay or post-pay items, eligibility, authorization and documentation processing and adjudication, special investigation and recovery.

41. The method of item 40, wherein suspicious providers or items result in items denial, items hold or items documentation request.

42. The method of item 41, wherein items denial, items hold or items documentation request may be implemented for either all items for a suspicious provider or a plurality of items meeting suspicious features for a suspicious provider.

43. The method of item 19, wherein the set of actions to be executed include the generation of a ranking of the plurality of providers or healthcare items and generation of a list of providers or healthcare items that are flagged as suspicious.

44. The method of item 19, wherein the set of actions to be executed include the generation of a list of the suspiciousness scores for the plurality of providers or healthcare items and features of suspicious activity for each provider.

45. The method of item 19, further comprising display of the actions to be executed.

46. The method of item 19, further comprising making the actions to be executed available through an application programmatic interface.

47. The method of item 19, wherein factorization is performed using graph-based features.

48. A computer-implemented method for automatically detecting anomalous healthcare providers and anomalous healthcare items, comprising:

in a first pipeline corresponding to a first set of care provision characteristics:

constructing, based on the first set of care provision characteristics, a first data structure based on healthcare items data of a plurality of healthcare providers;

automatically performing anomaly detection on the first data structure to obtain a set of data structures, wherein the set of data structures is indicative of one or more common patterns among the plurality of healthcare providers;

automatically, based on the set of data structures, obtaining a second data structure, wherein the second data structure is indicative of deviations by the plurality of healthcare providers from the one or more common patterns;

calculating, based on the second data structure, a score for a particular provider of the plurality of providers or a particular healthcare item of a plurality of healthcare items, wherein the score is indicative of an amount of deviation of the particular provider or the particular item from the one or more common patterns when providing the first care provision type;

causing a set of actions to be executed based on the score.

49. The method of item 48, wherein anomaly detection is performed using a one-class support vector machine, support vector data description, isolation forest, nearest-neighbor based techniques, histogram-based techniques, clustering-based techniques and attribute-wise learning for scoring outliers.

50. The method of item 48, wherein anomaly detection is performed using graph-based features.

51. The method of item 48, wherein anomaly detection is performed using a rule-based engine.

52. The method of item 48, wherein the care provision characteristics include diagnostic information, procedural information, setting information, scheduling information, referral information, location information, ownership information and combinations thereof.

53. The method of item 48, further comprising: receiving a user input indicative of a specialty, wherein the plurality of providers is selected based on the specialty.

54. The method of item 48, further comprising: receiving a user input indicative of a geography, wherein the plurality of providers is selected based on the geography.

55. The method of item 48, further comprising: receiving a user input indicative of a line of business, such as Medicare, Medicaid, Commercial, Family, Individual or Employer health insurance, wherein the plurality of providers is selected based on the line of business.

56. The method of item 48, wherein the score is a first score, the method further comprising:

in a second pipeline corresponding to a second set of care provision characteristics:

constructing, based on the second set of care provision characteristics, a third data structure based on healthcare items data of the plurality of healthcare providers;

calculating, based on the third data structure, a second score for the particular provider of the plurality of providers or the particular healthcare item of a plurality of healthcare items, wherein the score is indicative of an amount of deviation by the particular provider or the particular item from the most common patterns when providing the second care provision type;

calculating an overall score for the particular provider or the particular item based on the first score and the second score; and causing a set of actions to be executed based on the overall score.

57. The method of item 48, wherein the set of actions to be executed include pre-pay or post-pay items, eligibility, authorization and documentation processing and adjudication, special investigation and recovery.

58. The method of item 57, wherein suspicious providers or items result in items denial, items hold or items documentation request.

59. The method of item 58, wherein items denial, items hold or items documentation request may be implemented for either all items for a suspicious provider or a plurality of items meeting suspicious features for a suspicious provider.

60. The method of item 48, wherein the set of actions to be executed include the generation of a ranking of the plurality of providers or healthcare items and generation of a list of providers or healthcare items that are flagged as suspicious.

61. The method of item 48, wherein the set of actions to be executed include the generation of a list of the suspiciousness scores for the plurality of providers or healthcare items and features of suspicious activity for each provider.

62. An electronic device, comprising:

one or more processors;

a memory; and one or more programs, wherein the one or more programs are stored in the memory and configured to be executed by the one or more processors, the one or more programs including instructions for:

in a first pipeline corresponding to a first set of care provision characteristics:

constructing, based on the first set of care provision characteristics, a first data structure based on healthcare items data of a plurality of healthcare providers;

automatically performing factorization on the first data structure to obtain a set of data structures, wherein the set of data structures is indicative of the one or more common patterns among the plurality of healthcare providers;

automatically, based on the set of data structures, obtaining a second data structure, wherein the second data structure is indicative of deviations by the plurality of healthcare providers from the one or more common patterns;

calculating, based on the second data structure, a score for a particular provider of the plurality of providers or a particular healthcare item of a plurality of healthcare items, wherein the score is indicative of an amount of deviation of the particular provider or the particular item from the one or more common patterns when providing the first care provision type;

causing a set of actions to be executed based on the score.

63. A non-transitory computer-readable storage medium storing one or more programs, the one or more programs comprising instructions, which when executed by one or more processors of an electronic device, cause the electronic device to:

in a first pipeline corresponding to a first set of care provision characteristics:

constructing, based on the first set of care provision characteristics, a first data structure based on healthcare items data of a plurality of healthcare providers;

automatically performing factorization on the first data structure to obtain a set of data structures, wherein the set of data structures is indicative of the one or more common patterns among the plurality of healthcare providers;

automatically, based on the set of data structures, obtaining a second data structure, wherein the second data structure is indicative of deviations by the plurality of healthcare providers from the one or more common patterns;

calculating, based on the second data structure, a score for a particular provider of the plurality of providers or a particular healthcare item of a plurality of healthcare items, wherein the score is indicative of an amount of deviation of the particular provider or the particular item from the one or more common patterns when providing the first care provision type;

causing a set of actions to be executed based on the score.

64. An electronic device, comprising:

one or more processors;

a memory; and one or more programs, wherein the one or more programs are stored in the memory and configured to be executed by the one or more processors, the one or more programs including instructions for:

in a first pipeline corresponding to a first set of care provision characteristics:

constructing, based on the first set of care provision characteristics, a first data structure based on healthcare items data of a plurality of healthcare providers;

automatically performing anomaly detection on the first data structure to obtain a set of data structures, wherein the set of data structures is indicative of one or more common patterns among the plurality of healthcare providers;

automatically, based on the set of data structures, obtaining a second data structure, wherein the second data structure is indicative of deviations by the plurality of healthcare providers from the one or more common patterns;

calculating, based on the second data structure, a score for a particular provider of the plurality of providers or a particular healthcare item of a plurality of healthcare items, wherein the score is indicative of an amount of deviation of the particular provider or the particular item from the one or more common patterns when providing the first care provision type;

causing a set of actions to be executed based on the score.

65. A non-transitory computer-readable storage medium storing one or more programs, the one or more programs comprising instructions, which when executed by one or more processors of an electronic device, cause the electronic device to:

in a first pipeline corresponding to a first set of care provision characteristics:

constructing, based on the first set of care provision characteristics, a first data structure based on healthcare items data of a plurality of healthcare providers;

automatically performing anomaly detection on the first data structure to obtain a set of data structures, wherein the set of data structures is indicative of one or more common patterns among the plurality of healthcare providers;

automatically, based on the set of data structures, obtaining a second data structure, wherein the second data structure is indicative of deviations by the plurality of healthcare providers from the one or more common patterns;

calculating, based on the second data structure, a score for a particular provider of the plurality of providers or a particular healthcare item of a plurality of healthcare items, wherein the score is indicative of an amount of deviation of the particular provider or the particular item from the one or more common patterns when providing the first care provision type;

causing a set of actions to be executed based on the score.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A computer-implemented method for using machine-learning to detect anomalous healthcare providers, comprising:

receiving, by one or more processors, medical data of a plurality of healthcare providers;

receiving, by the one or more processors, a selected target rank, wherein selecting the target rank comprises:

for each candidate target rank of a plurality of candidate target ranks:

determining a plurality of solutions, the solutions associated with different initializations, and determining an approximation error associated with the plurality of solutions, wherein the approximate error is indicative of solution reproducibility, and selecting a target rank from the plurality of candidate target ranks in accordance with a determination that the selected target rank is associated with a minimum approximation error to determine reproducible solutions independent of the random initialization used;

obtaining, by the one or more processors, a subset of the medical data based on a first care provision type and the selected target rank;

constructing, by the one or more processors, a first tensor based on the subset of the medical data, wherein the first tensor comprises a first dimension related to the plurality of healthcare providers, a second dimension related to a plurality of diagnoses, and a third dimension related to treatment by the plurality of healthcare providers related to the plurality of diagnoses;

executing, by the one or more processors, a tensor factorization algorithm to decompose the first tensor into a plurality of data structures, wherein:

the plurality of data structures is indicative of one or more common patterns among the plurality of healthcare providers, and the selected target rank defines a size of the tensor factorization algorithm;

reconstructing, by the one or more processors, the first tensor by generating a second tensor using the plurality of data structures, wherein the second tensor has the same dimensions as the first tensor;

calculating, based on the first tensor and the second tensor, a score for a particular provider of the plurality of providers, wherein the score is indicative of an amount of deviation of the particular provider from the one or more common patterns when providing the first care provision type; and providing a recommendation regarding the particular provider based on the score.

2. The computer-implemented method of claim 1, wherein the tensor factorization algorithm is an unsupervised machine-learning algorithm.

3. The computer-implemented method of claim 1, wherein the first tensor comprises a multi-dimensional array, wherein each cell is an exact or normalized count for each provider or a combination of providers of an occurrence of a specific combination of care provision characteristics.

4. The computer-implemented method of claim 3, wherein the first tensor comprises a three-dimensional array, wherein each (i,j,k) cell is the number of times a k-th provider billed for a i-th procedure code using a i-th principal diagnosis.

5. The computer-implemented method of claim 1, wherein the plurality of data structures corresponds to a plurality of rank-1 tensors, and wherein each rank-1 tensor of the plurality of rank-1 tensors is stored as one or more vectors.

6. The computer-implemented method of claim 1, wherein the factorization algorithm is a CANDECOMP/PARAFAC (CP) tensor factorization algorithm.

7. The computer-implemented method of claim 1, further comprising: receiving a user input indicative of a specialty, wherein the plurality of providers is selected based on the specialty.

8. The computer-implemented method of claim 1, wherein the second tensor comprises a reconstruction error tensor.

9. The computer-implemented method of claim 8, further comprising:

identifying a slice of the reconstruction error tensor, wherein the slice corresponds to the particular provider; and calculating the score for the particular provider based on the slice.

10. The computer-implemented method of claim 9, further comprising calculating scores of features or their co-occurrence with other features based on the slice.

11. The computer-implemented method of claim 9, wherein the score is a maximum value of the slice, an average of the slice, or a combination thereof.

12. The computer-implemented method of claim 1, wherein the first tensor is a feature matrix.

13. The computer-implemented method of claim 1, wherein the score is a first score and the subset is a first subset, the method further comprising:

obtaining, by the one or more processors, a second subset of the medical data based on a second care provision type; and calculating a second score for the particular provider of the plurality of providers, wherein the score is indicative of an amount of deviation by the particular provider from the one or more common patterns when providing the second care provision type;

calculating an overall score for the particular provider based on the first score and the second score; and causing display of the particular provider based on the overall score.

14. The computer-implemented method of claim 1, further comprising automatically ranking the plurality of providers.

15. The computer-implemented method of claim 1, wherein the first care provision type comprises: delivering services, referring services, scheduling services, or sourcing patients to locations.

16. The computer-implemented method of claim 1, further comprising:

obtaining, based on the second tensor, one or more anomalous features corresponding to the particular provider;

receiving data corresponding to a healthcare claim by the particular provider;

comparing the one or more anomalous features with the healthcare claim; and flagging the healthcare claim if there is an overlap between the healthcare claim and the one or more anomalous features.

17. An electronic device, comprising:

one or more processors;

a memory; and one or more programs, wherein the one or more programs are stored in the memory and configured to be executed by the one or more processors, the one or more programs including instructions for:

receiving, by one or more processors, medical data of a plurality of healthcare providers;

receiving, by the one or more processors, a selected target rank, wherein selecting the target rank comprises:

for each candidate target rank of a plurality of candidate target ranks:

determining a plurality of solutions, the solutions associated with different initializations, and determining an approximation error associated with the plurality of solutions, wherein the approximate error is indicative of solution reproducibility, and selecting a target rank from the plurality of candidate target ranks in accordance with a determination that the selected target rank is associated with a minimum approximation error to determine reproducible solutions independent of the random initialization used;

obtaining, by the one or more processors, a subset of the medical data based on a first care provision type and the selected target rank;

constructing, by the one or more processors, a first tensor based on the subset of the medical data, wherein the first tensor comprises a first dimension related to the plurality of healthcare providers, a second dimension related to a plurality of diagnoses, and a third dimension related to treatment by the plurality of healthcare providers related to the plurality of diagnoses;

executing, by the one or more processors, algorithm to decompose the first tensor into a plurality of data structures, wherein:

the plurality of data structures is indicative of one or more common patterns among the plurality of healthcare providers, and the selected target rank defines a size of the tensor factorization algorithm;

reconstructing, by the one or more processors, the first tensor by generating a second tensor using the plurality of data structures, wherein the second tensor has the same dimensions as the first tensor;

calculating, based on the first tensor and the second tensor, a score for a particular provider of the plurality of providers, wherein the score is indicative of an amount of deviation of the particular provider from the one or more common patterns when providing the first care provision type; and providing a recommendation regarding the particular provider based on the score.

18. A non-transitory computer-readable storage medium storing one or more programs, the one or more programs comprising instructions, which when executed by one or more processors of an electronic device having a display, cause the electronic device to:

receiving, by one or more processors, medical data of a plurality of healthcare providers;

receiving, by the one or more processors, a selected target rank, wherein selecting the target rank comprises:

for each candidate target rank of a plurality of candidate target ranks:

determining a plurality of solutions, the solutions associated with different initializations, and determining an approximation error associated with the plurality of solutions, wherein the approximate error is indicative of solution reproducibility, and selecting a target rank from the plurality of candidate target ranks in accordance with a determination that the selected target rank is associated with a minimum approximation error to determine reproducible solutions independent of the random initialization used;

obtaining, by the one or more processors, a subset of the medical data based on a first care provision type and the selected target rank;

constructing, by the one or more processors, a first tensor based on the subset of the medical data, wherein the first tensor comprises a first dimension related to the plurality of healthcare providers, a second dimension related to a plurality of diagnoses, and a third dimension related to treatment by the plurality of healthcare providers related to the plurality of diagnoses;

executing, by the one or more processors a tensor factorization algorithm to decompose the first tensor into a plurality of data structures, wherein:

the plurality of data structures is indicative of one or more common patterns among the plurality of healthcare providers, and the selected target rank defines a size of the tensor factorization algorithm;

reconstructing, by the one or more processors, the first tensor by generating a second tensor using the plurality of data structures, wherein the second tensor has the same dimensions as the first tensor;

calculating, based on the first tensor and the second tensor, a score for a particular provider of the plurality of providers, wherein the score is indicative of an amount of deviation of the particular provider from the one or more common patterns when providing the first care provision type; and providing a recommendation regarding the particular provider based on the score.

* * * * *